(12) United States Patent
Womble et al.

(10) Patent No.: US 10,555,498 B2
(45) Date of Patent: Feb. 11, 2020

(54) METHOD AND SYSTEM FOR REMOTE MONITORING, CARE AND MAINTENANCE OF ANIMALS

(71) Applicants: Krystalka R. Womble, Dallas, TX (US); Robert L. Piccioni, Rowlett, TX (US)

(72) Inventors: Krystalka R. Womble, Dallas, TX (US); Robert L. Piccioni, Rowlett, TX (US)

(73) Assignee: Botsitter, LLC, Rowlett, TX (US)

( * ) Notice: Subject to any disclaimer, the term of this patent is extended or adjusted under 35 U.S.C. 154(b) by 303 days.

(21) Appl. No.: 15/598,203

(22) Filed: May 17, 2017

(65) Prior Publication Data
US 2017/0251633 A1    Sep. 7, 2017

Related U.S. Application Data

(63) Continuation-in-part of application No. 15/365,895, filed on Nov. 30, 2016, now Pat. No. 9,936,680, (Continued)

(51) Int. Cl.
*A01K 29/00* (2006.01)
*A01K 5/02* (2006.01)
(Continued)

(52) U.S. Cl.
CPC ............... *A01K 5/02* (2013.01); *A01K 7/02* (2013.01); *A61B 34/10* (2016.02); *A61M 5/31* (2013.01); *A01K 15/021* (2013.01); *A01K 29/005* (2013.01)

(58) Field of Classification Search
CPC .. A01K 29/005; A01K 11/008; A01K 15/021; A01K 27/00; A01K 11/006; B64C 2201/12
(Continued)

(56) References Cited

U.S. PATENT DOCUMENTS 3,630,174 A * 12/1971 Runkle .................. A01K 1/031
119/419
4,526,133 A * 7/1985 LoMaglio .............. A01K 1/031
119/419
(Continued)

OTHER PUBLICATIONS

Saenz, A., "Remote Controlled Robot Pet Sitter," SingularityHub, https://singularityhub.com/2009/11/02/remote-controlled-robot-pet-sitter/, Nov. 2, 2009, 2 pages.
(Continued)

*Primary Examiner* — Yvonne R Abbott-Lewis
(74) *Attorney, Agent, or Firm* — Wei Wei Jeang; Grable Martin Fulton PLLC

(57) ABSTRACT

A system for remote care of an animal includes a robotic animal caregiver that has a housing, a wireless data communication system disposed within the housing and wirelessly communicatively coupled with an external data communications system, and a microprocessor in communication with the wireless data communication system disposed within the housing. The system further includes an aerial drone wirelessly communicatively coupled to the wireless data communication system of the robotic animal caregiver. The aerial drone includes a microprocessor, a wireless communication module, a video camera, the aerial drone configured to act in response to instructions issued by the microprocessor of the robotic animal caregiver.

32 Claims, 31 Drawing Sheets

Related U.S. Application Data which is a continuation-in-part of application No. 14/823,859, filed on Aug. 11, 2015, now Pat. No. 9,538,728, which is a continuation-in-part of application No. 14/191,244, filed on Feb. 26, 2014, now Pat. No. 9,131,660, which is a continuation of application No. 13/892,292, filed on May 12, 2013, now Pat. No. 8,707,900.

(60) Provisional application No. 61/848,437, filed on Jan. 4, 2013, provisional application No. 61/702,856, filed on Sep. 19, 2012.

(51) Int. Cl.
*A61B 34/10* (2016.01)
*A61M 5/31* (2006.01)
*A01K 7/02* (2006.01)
*A01K 15/02* (2006.01)

(58) Field of Classification Search
USPC .............. 119/712, 719, 720, 51.01, 51.5
See application file for complete search history.

(56) References Cited

U.S. PATENT DOCUMENTS

| | | | |
|---|---|---|---|
| 5,081,955 A * | 1/1992 | Yoneda | A01K 1/031 119/417 |
| 5,349,924 A * | 9/1994 | Hooper, Jr. | A01K 1/0245 119/472 |
| 5,467,734 A * | 11/1995 | Ho | A01K 1/0236 119/496 |
| 6,425,347 B1 * | 7/2002 | Bogner | A61D 3/00 119/315 |
| 6,779,486 B2 | 8/2004 | Vaags | |
| 7,036,458 B1 * | 5/2006 | Stornant | A01K 1/011 119/453 |
| 7,040,249 B1 | 5/2006 | Mushen | |
| D566,907 S * | 4/2008 | Barca | D30/109 |
| 7,513,218 B1 | 4/2009 | Handley et al. | |
| 7,997,234 B1 * | 8/2011 | Hughey | A01K 1/034 119/496 |
| 8,113,148 B2 | 2/2012 | Chem | |
| 8,297,233 B2 | 10/2012 | Rich et al. | |
| 9,661,827 B1 * | 5/2017 | Shen | A01K 15/021 |
| 9,804,596 B1 * | 10/2017 | Slavin | G05D 1/0022 |
| 9,861,075 B2 * | 1/2018 | Shen | A01K 15/021 |
| 10,242,547 B1 * | 3/2019 | Struhsaker | H04L 67/125 |
| 2005/0284405 A1 * | 12/2005 | Pomakoy-Poole | A01K 1/0245 119/497 |
| 2009/0223463 A1 * | 9/2009 | Chem | A01K 1/033 119/482 |
| 2012/0199080 A1 * | 8/2012 | Siddons | A01K 1/033 119/448 |
| 2016/0057968 A1 * | 3/2016 | Chandler | A01K 1/0272 119/497 |
| 2017/0188545 A1 * | 7/2017 | Bivens | B64C 39/024 |
| 2017/0238505 A1 * | 8/2017 | Gordon | A01K 15/021 |
| 2018/0027772 A1 * | 2/2018 | Gordon | A01K 15/023 |
| 2018/0116170 A1 * | 5/2018 | Joshi | H04N 7/141 |
| 2018/0146645 A1 * | 5/2018 | Arbel | A61B 5/103 |

OTHER PUBLICATIONS

The Ashes, "Mint Pet robot keeps an eye on your pet's moves," Technology, Science and other news, http://cciash.com/mint-pet-robot-keeps-an-eye-on-your-pets-moves/, Sep. 7, 2009, 2 pages.

* cited by examiner

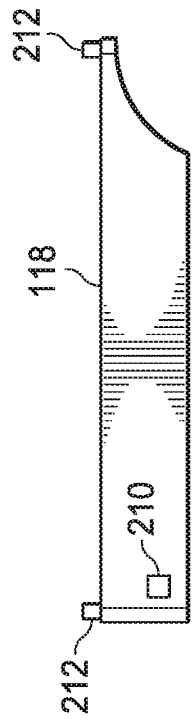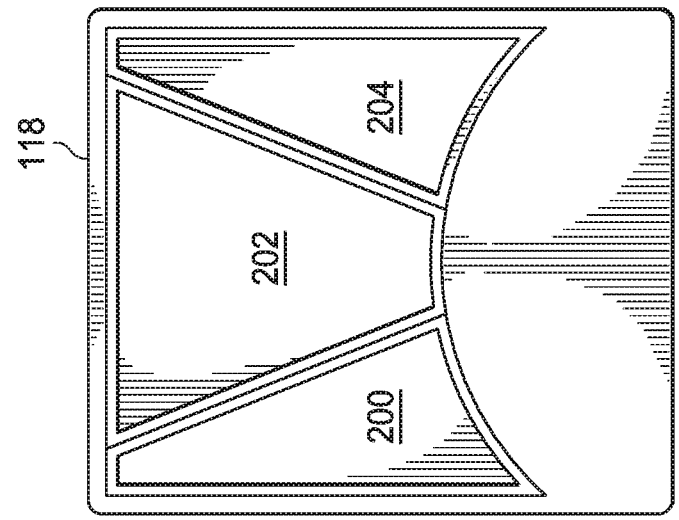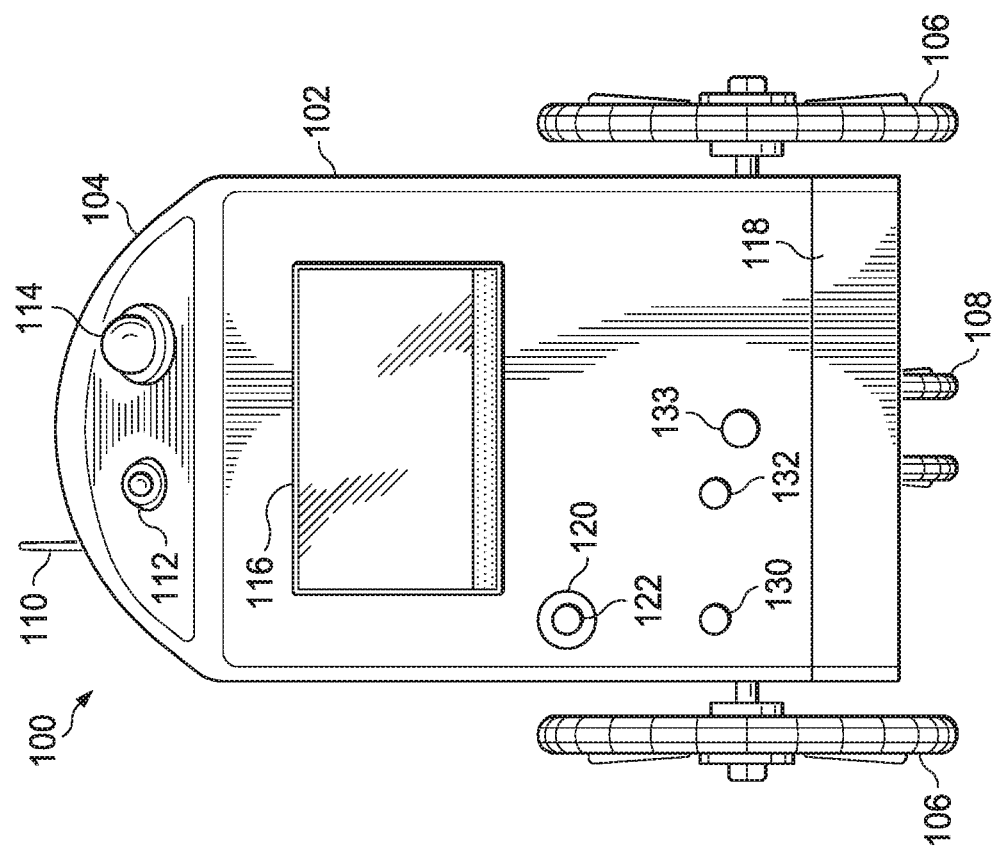

METHOD AND SYSTEM FOR REMOTE MONITORING, CARE AND MAINTENANCE OF ANIMALS

RELATED APPLICATIONS

This patent application is a continuation-in-part of U.S. patent application Ser. No. 15/365,895 filed Nov. 30, 2016, which is a continuation-in-part of U.S. patent application Ser. No. 14/823,859 filed on Aug. 11, 2015 (now U.S. Pat. No. 9,538,728), which is a continuation-in-part of U.S. application Ser. No. 14/191,244 filed on Feb. 26, 2014 (now U.S. Pat. No. 9,131,660), which is a continuation of U.S. patent application Ser. No. 13/892,292 filed on May 12, 2013 (now U.S. Pat. No. 8,707,900), which claims the benefit of U.S. Provisional Patent Application No. 61/848,437 filed Jan. 4, 2013 and U.S. Provisional Patent Application No. 61/702,856 filed Sep. 19, 2012. This patent application is also related to U.S. patent application Ser. Nos. 15/365,896 and 15/365,901, both filed on Nov. 30, 2016. All of the aforementioned patent applications are incorporated herein by reference.

TECHNICAL FIELD

The invention relates generally to mechanical systems and, more particularly, the invention relates to a remote controlled personal animal care device by using drone technology.

DESCRIPTION OF THE RELATED ART

As computers have grown increasingly important in today's society, humans have created animal care devices to automate and enhance various activities that have traditionally been performed manually. Domesticated pets, livestock animals and wild animals maintained in a controlled environment rely in great measure on the care and attention of humans to remain mentally and physically healthy and alert. Items that are assistive in nature to help owners maintain the wellbeing of their animals can provide some portion of such care and attention. Animal owners are often hampered in their attempts to properly care for their animals when the owner is required to be geographically distant from the place their animals are kept. In many cases, animal owners are required to contract with third-party providers to perform simple tasks related to feeding, watering and administering medications to animals when the animal owner is not physically present to do so. Indeed, each year, numerous animals die or are caused physical or emotional harm due to the lack of proper care by owners who are geographically removed from the animal or due to the inadvertent or purposeful oversight of third-party animal caregivers.

SUMMARY

An animal care system for remote care and maintenance of animals is presented. According to one embodiment of the present disclosure, the system includes a housing and a mobility portion coupled to the housing and operable to move the housing. The system further includes a wireless data communications system disposed with the housing and wirelessly communicatively coupled with an external data communications system and an electronic data processor disposed within the system and controlling the mobility portion. In addition, the system includes food, water and medicine storage portions disposed within the housing. Further, the system includes a removable tray coupled to the housing and disposed proximate to a lower portion of the housing, the tray having a food tray portion operable to receive food from the food storage portion, a water tray portion operable to receive water from the water storage portion and a medicine tray portion operable to receive medicine from the medicine storage portion and a docking portion fixedly coupled to the housing and disposed generally on a rear portion of the housing, and connectively coupled to the food, water and medicine storage portions. Also, the system includes an internal electronic fence transceiver in wireless communication with an external electronic fence transceiver, the internal electronic fence transceiver disposed generally within the housing and the external electronic fence transceiver disposed externally and remote from the housing, wherein the internal electronic fence transceiver activates the external electronic fence transceiver when the external electronic fence transceiver is at least a predetermined distance from the housing.

The system further includes an aerial drone wirelessly communicatively coupled to the robotic animal caregiver and configured to act in response to instructions issued by the robotic animal caregiver.

BRIEF DESCRIPTION OF THE DRAWINGS

A better understanding of the claimed subject matter can be obtained when the following detailed description of the disclosed embodiments is considered in conjunction with the following figures.

FIG. 1 is a diagram illustrating a front view of an animal care device 100 according to one embodiment of the present disclosure;

FIG. 2A is a side view of tray 118 according to one embodiment of device 100 according to one embodiment of the present disclosure;

FIG. 2B is a top view of tray 118 according to one embodiment of device 100 according to one embodiment of the present disclosure;

DESCRIPTION

Figure 3:
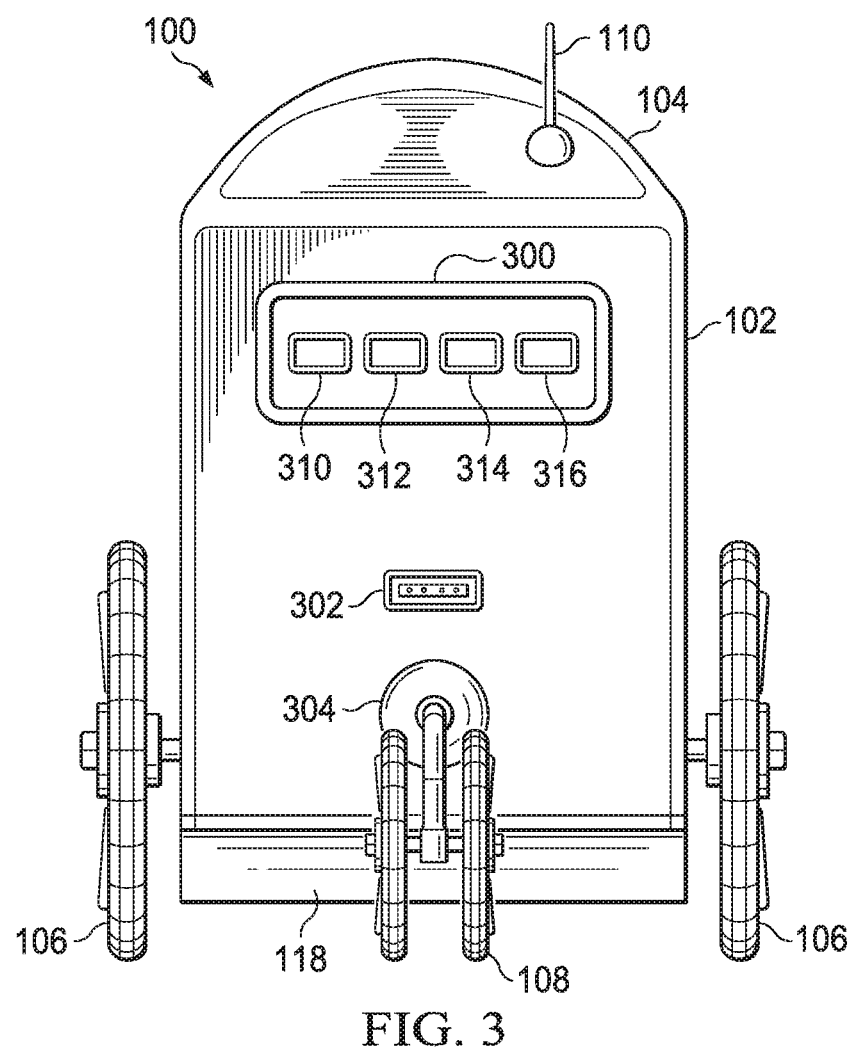
FIG. 3 is a rear view of device 100 according to one embodiment of the present disclosure.

Humans have been making use of animals for both productive purposes, such as food and labor, and as companions, such as domesticated dogs and cats, since the earliest days of recorded history. In order to make use of these animals, the animals are typically kept in controlled or semi-controlled environments, such as houses and fenced outdoor areas, in order to control the movements of the animals and to protect the animals from predators. As a result of placing the animals in such environments, the animal must rely upon human assistance and support in order to survive. For example, domestic dogs and cats rely upon their owners to provide food and water. In addition, humans often train the animals to behave in certain ways that require human assistance or support as the animals may be physically incapable of performing such actions directly. For example, a door may need to be opened for a dog to allow the dog to relieve itself outside and a cat litter box requires periodic cleaning by the owner. However, the time available to an owner to perform these activities may be limited or the owner may need to be in a physically distant location from the animal due to, for example, job responsibilities. A pet care robot may be used to perform various animal care tasks that normally are performed by humans. For example, a pet care robot may be capable of walking and playing with a domestic dog that lives in a residence, and providing food, water and medicine to the dog. In addition, the pet care robot may provide a video and audio link to allow the dog to see the dog's owner, even though the owner is physically distant from the dog.

FIG. 1 is a diagram illustrating a front view of an animal care device 100 according to one embodiment of the present disclosure. The animal care device 100, in various embodiments, provides various capabilities useful for providing care to an animal. For example, the animal care device 100 may walk a dog, provide food, water and medicine, or provide a video display showing a real-time or prerecorded video or image of the dog's owner. The animal care device 100 comprises a main body 102, an upper body 104, a pair of front wheels 106, a pair of rear wheels 108, a wireless system 110, a camera 112, a playing device 114, audio/video display 116, a tray 118, an arm 120, a scent emitter 130, a heat/cold emitter 132, and a secondary animal waste detection sensor system 133.

Main body 102 comprises the main physical support structure for the animal care device 100. In the disclosed embodiment, main body 102 is generally cylindrical in shape and provides mounting support for front wheels 106, rear wheels 108, tray 118 and display 116. Enclosed within main body 102 may be various electronic, electro-mechanical and mechanical systems for operation of animal care device 100 as described in greater detail below. Main body 102 may be formed from any suitable material, such as steel, aluminum, plastic or other composites as desired. For example, an animal care device 100 for use with a horse may require use of stronger, heavier or more costly materials than one for use with domesticated house pets. Main body 102 may alternatively be of other suitable shapes. Front wheels 106 are coupled to main body 102 and may be used to move and/or steer animal care device 100. Rear wheels 108 are coupled to main body 102 and may alternatively or in addition to front wheels 106 to move and/or steer animal care device 100. The illustration of the pair of front wheels 106 and rear wheels 108 represent only a single embodiment of device 100, alternatively, various other drive systems may be used in various suitable combinations for the use of device 100. For example, a single rear wheel 108 may be used and rear and front wheels 108 and 106 may be combined or organized in some other suitable format, such as four wheels with a steering system similar to a passenger vehicle. Also, device 100 may be a tracked vehicle for operation outdoors or in hostile environments, such as snow. Device 100 may further comprise electronic data processing capabilities, such as using a central processing unit (CPU) coupled to memory (not shown), in order to store and execute computer programming instructions to control device 100.

In one embodiment, upper body 104 comprises a generally dome shaped element removably or fixably coupled to main body 102. More specifically, upper body 104 and main body 102 may be formed as a single physical element or may represent separate physical elements that are coupled together. For example, upper body 104 may be designed to be removed from main body 102 to allow access to the interior of main body 102 for maintenance purposes. Upper body 104 may also be of other suitable shapes in various embodiments. Upper body 104 provides support and mounting locations for wireless system 110, camera 112 and toy 114. Enclosed within upper body 104 may be electrical, electro-mechanical and/or mechanical elements in support of device 100 as described in greater detail below. For example, portions of wireless system 110 may be disposed within the interior of upper body 104. Upper body 104 may further be operable to rotate around a vertical axis independently of main body 102, for example, to allow camera 112 to be pointed in various directions without rotating main body 102 as well. In general, similar to main body 102, upper body 104 may be of a suitable shape and be made of suitable materials for a particular embodiment of device 100.

Wireless system 110 comprises one or more of a global positioning system (GPS) transmitter/receiver, a wireless audio and/or data communications transmitter/receiver, such as an IEEE 802.11a/b/g/n or cellular data connection, Bluetooth transmitter/receiver, and a wireless fence system and suitable associated hardware, such as an antenna.

Camera 112 comprises any suitable still and/or video camera for generating an image and communicating the image to the wireless system 110.

Toy 114 comprises a ball at the end of cord that is operable to be ejected away from device 100 and retracted back to device 100. For example, a rubber ball may be used that is thrown for a dog to chase so that an owner can play with their dog from a remote location. Alternatively, toy 114 may comprise an imitation mouse that may be used to entertain a cat. In general, toy 114 may comprise any suitable object that is tethered to device 100 and ejected away from, and returned to, device 100 for interaction with an animal. Alternatively, toy 114 may be any form of device that can amuse the animal, such as a light or laser.

Tray 118 comprises a tray that is detachable from and re-attachable to device 100 in order to serve food, water and/or medicines to an animal. In one embodiment, device 100 lowers itself so that the bottom of tray 118 is sitting upon the ground and then releases tray 118. Device 100 would then raise itself back to a normal operating height and move away from tray 118 to allow an animal to eat and drink from the tray. Device 100 would later return to tray 118, lower itself such that the bottom of main body 102 is generally in contact with the top of tray 118, and reattach tray 118 to main body 102. Tray 118 may alternatively be removably coupled to main body 102 in any suitable way. For example, tray 118 may slide into and out of a cavity in main body 102, for example using a lip on tray 118 that engages with a track below main body 102. Tray 118 is described in more detail in association with FIGS. 2A and 2B below.

Arm 120 comprises a movable arm operable to deliver a payload 122 to an animal. In one embodiment, payload 122 comprises a syringe for providing an injection to an animal and arm 120 is capable of articulation appropriate for providing an injection. For example, an animal may be diabetic and require an insulin injection. For another example, payload 122 may comprise an injectable or spray-based tick repellent.

Scent emitter 130 comprises a suitable system for emitting a predetermined scent. As many animals rely on scent, as opposed to visual or auditory cues, device 100 provides the caregiver the ability to provide one or more scents as appropriate for the animal under care. For example, in one embodiment, scent emitter 130 may simply comprise a cavity with a fan where an object, such as clothing worn by a caregiver, is placed to provide a familiar scent to an animal. Alternatively, scent emitter 130 may comprise more complex systems using chemicals or concentrated scents that may be sprayed or otherwise emitted from device 100 as desired by a caregiver. Scent emitter 130 may operate independently according to predetermined criteria, such as time of day, and/or may be under direct remote control by the caregiver.

According to one embodiment of the present invention, a heat/cold emitter 132 may be included with device 100, such as on main body 102. Heat/cold emitter comprises one or both of a heater and/or air conditioner operable to heat and/or cool an area around device 100. For example, in harsh environments it may be necessary to provide environmental controls for an animal, such as a pregnant horse that lives outside during unexpected weather changes or a domestic pet in the event of a power failure at a house.

Animal care device 100 also includes a secondary animal waste detection system 133 that may deploy one or more technology based on radar, ground anomaly detection, video analysis, ultrasound technology, image recognition, scent recognition, heat signature detection, chemical detection, and detection of one or more predetermined substance or device. The secondary animal waste detection system 133 may be configured to detect a substance that is used to pre-treat the deposited feces, for example. Alternatively, the animal may be fed food that contains an additive substance and/or device that can be detected by the secondary animal waste detection system 133. The additive substance can be a specific chemical composition, a metal, and/or a micro-tag (which may be based on RFID technology or another technology now known or to be developed).

FIG. 2a is a side view of tray 118 according to one embodiment of device 100. FIG. 2b is a top view of tray 118 according to one embodiment of device 100. As shown in FIG. 2a, in one embodiment, tray 118 may comprise a cutout in the rear portion to account for movement of rear wheels 108. In one embodiment, tray 118 further comprises at least one post 212 engageable within main body 102 to hold and release tray 118 from main body 102. For example, posts 212 may engage with a solenoid within main body 102 to couple tray 118 to main body 102 and retain tray 118 with device 100. In this example, the solenoids may be activated to latch with posts 212 or may use friction to retain tray 118, while the deactivation of the solenoids would allow tray 118 to be released from a lower portion of main body 102. Alternatively, tray 118 may be releasably coupled to main body 102 using a magnetic retention and release system or other suitable electrical, electro-mechanical or mechanical systems. As shown in FIG. 2b, tray 118 comprises a food portion 200, a water portion 202 and a medicine portion 204. Food portion 200 receives food from device 100 and contains the food for consumption by an animal. Water portion 202 receives water or other liquids from device 100 and contains the water for consumption by an animal. Medicine portion 204 receives medicine in solid or liquid form from device 100 and contains the medicine for consumption by an animal. For example, tray 118 may be a plastic tray with open-topped compartments acting as portions 200, 202 and 204.

In one embodiment, tray 118 may further comprise sensor 210. Sensor 210 is operable to detect that one or more of portions 200, 202 and/or 204 are in need of refilling and signaling to device 100 that tray 118 needs refilling.

Figure 4:
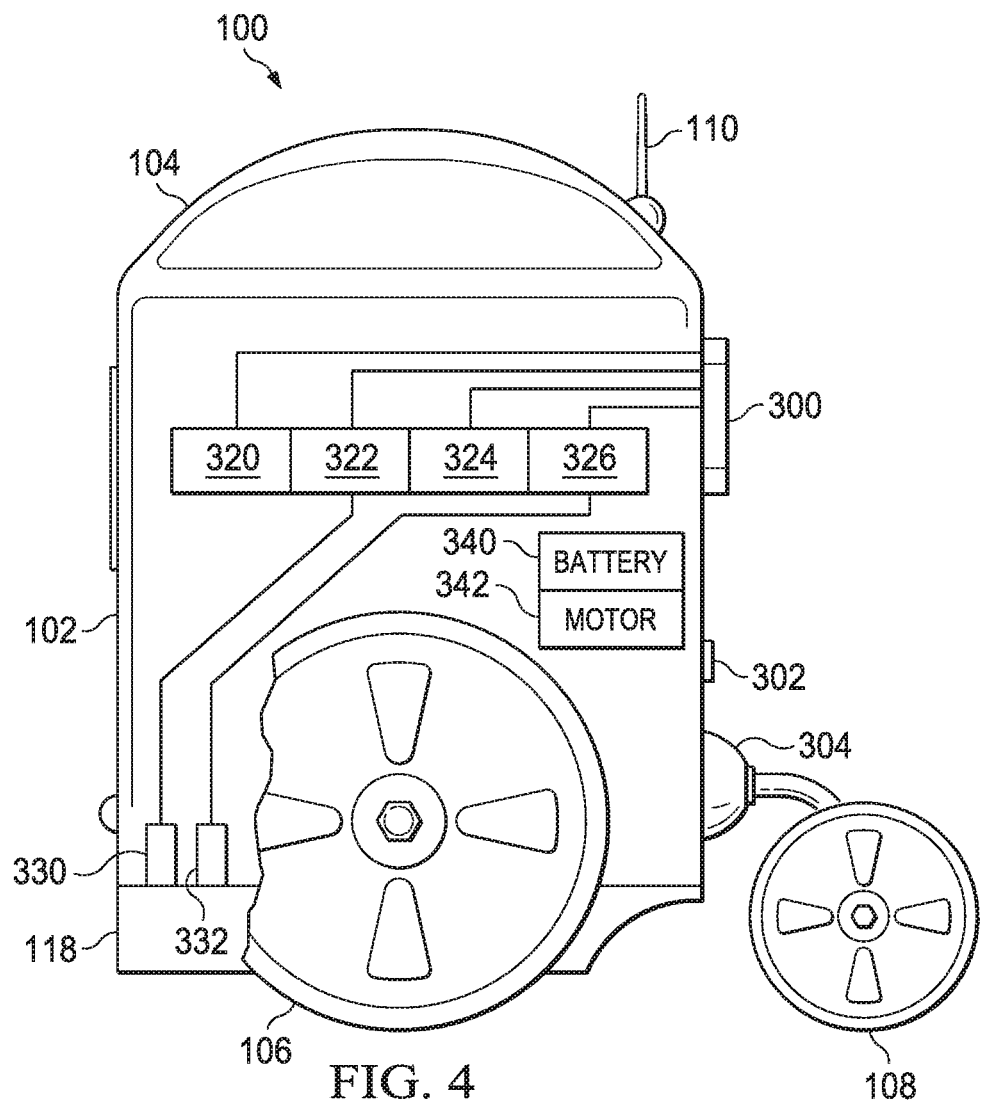
FIG. 4 is a side view of device 100 according to one embodiment of the present disclosure.

FIG. 3 is a rear view of device 100 according to one embodiment of the present disclosure. FIG. 4 is a side view of device 100 according to one embodiment of the present disclosure. FIGS. 3 and 4 are described together for greater clarity. Device 100 further comprises a plurality of charging ports 300, an electrical port 302, a directional system 304, a water bin 320, a food bin 322, a medicine bin 324, a waste bin 326, a cleaning nozzle 330, a water suction nozzle 332, a battery 340 and a motor 342. Charging ports 300 comprise a food port 310, a water port 312, a medicine port 314 and a waste port 316. Electrical port 302 comprises suitable electrical interfaces for recharging device 100 from a power source, such as an electrical grid tied receptacle, solar panels, wind power or other suitable electrical power sources.

Food port 310 comprises a receptacle operable to receive animal feed to refill device 100 with feed for dispensing to an animal on tray 118. Food received from food port 310 is stored in food bin 320. Food bin 320 comprises any suitable container for solid or liquid items, is disposed within main body 102 and is coupled to food port 310 via a suitable tube or pipe. In one embodiment, food bin 320 may be removed from main body 102 by opening upper body 104. For example, food bin 320 may be removed for cleaning or manual refilling.

Water port 312 comprises a receptacle operable to receive water to refill device 100 for dispensing to an animal on tray 118. Water received from water port 311 is stored in water bin 322. Water bin 322 comprises any suitable container for liquid items, is disposed within main body 102 and is coupled to water port 312 via a suitable tube or pipe. In one embodiment, water bin 322 may be removed from main body 102 by opening upper body 104.

Medicine port 314 comprises a receptacle operable to receive medicines to refill device 100 for dispensing to an animal on tray 118. Medicine received from medicine port 314 is stored in medicine bin 324. Medicine bin 324 comprises any suitable container for solid or liquid items, is disposed within main body 102 and is coupled to medicine port 314 via a suitable tube or pipe. In one embodiment, medicine bin 324 may be removed from main body 102 by opening upper body 104. In another embodiment, medicine bin 324 may be coupled to or accessible by payload 122 to in order to refill a syringe, for example, via a tube through arm 120.

In addition, one or more of bins 320, 322, 324 and/or 326 may be refrigerated or heated as needed. For example, medicine bin 324 may be required to be kept refrigerated to keep medicine from spoiling.

Waste bin 326 receives water and other debris from suction nozzle 332 for storage until the contents of waste bin 326 are removed from device 100 via waste port 316. Waste port 316 is coupled to waste bin 326 via a suitable tube or pipe to allow extraction of the contents of waste bin 326.

Cleaning nozzle 330 comprises a device operable to expel water at a suitable level of pressure to clean tray 118. Cleaning nozzle 330 is coupled to water bin 322 via a suitable tube or pipe. For example, cleaning nozzle 330 may comprise a water-spraying device that sprays water under pressure onto tray 118. In one embodiment, cleaning nozzle 330 is of a suitable size and located within main body 102 at a location such that cleaning nozzle 330 sprays water onto tray 118. In another example, cleaning nozzle 330 may be operable to move within main body 102 in order to clean portions of tray 118. In addition, cleaning nozzle 330 may represent multiple cleaning elements, such as multiple sprayers, for cleaning tray 118 in various embodiments. For example, nozzle 330 may comprise or include a heated air emitter to dry tray 118 or other surfaces. Further, in one embodiment, a bin for a cleaning solution may be further coupled between water bin 322 and cleaning nozzle 330. In yet another embodiment, nozzle 330 may be used to clean areas under device 100 after tray 118 has been detached, for example, to clean a floor.

Suction nozzle 332 comprises a device operable to remove water and/or debris from tray 118 and deposit the removed water and/or debris in waste bin 328 via a suitable tube or pipe. For example, as cleaning nozzle 330 is spraying water to clean tray 118, suction nozzle 332 is removing the used water from tray 118. In general, suction nozzle 332 comprises any suitable device or devices operable to remove used water and used cleaning fluids from tray 118. In various embodiments, cleaning nozzle 330 and suction nozzle 332 may require the use of pumps (not shown) to generate suitable levels of water pressure for cleaning tray 118 and suction force to remove liquid and/or solid debris. For example, in one embodiment, suction nozzle 332 and cleaning nozzle 330 may be used to clean surfaces other than tray 118, such as debris or waste on a floor or other surface. This embodiment may require the release of tray 118 prior to performing such cleaning activities.

Battery 340 comprises any suitable battery technology, such as lead-acid, NiMH, Lithium-Ion and NiCad, operable to power motor 342 and device 100 generally. Battery 340 is electrically coupled to charging port 300 and is recharged when charging port 300 is connected to an external power source. Battery 340 is sized as suitable for the animal being cared for by device 100 and the related power demands of motor 342 and the various electronics associated with device 100, such as wireless communications system 110. For example, an animal care device 100 for taking care of horses in an outdoor field may be larger and require a stronger motor 342 and battery 340 to deal with the relatively harsh environment. In contrast, an animal care device 100 that is primarily designed for use with a household pet may require a less powerful motor 342 and battery 340.

Motor 342 comprises a suitable motor for driving front wheels 106 and/or rear wheels 108, depending on the embodiment of device 100, to allow device 100 to move from place to place. In one embodiment, motor 342 comprises an electric motor powered by battery 340.

Directional system 304 comprises a movable joint operable to turn rear wheels 108 and to lower device 100. In one embodiment, rear wheels 108 provide directional control for device 100, while front wheels 106 provide the driving force to move device 100. In addition, to order to release tray 118 on the ground, device 100 may lower itself so that the bottom of tray 118 is on or near the ground before releasing tray 118. In this embodiment, directional system 304 pivots the rear wheels 108 to lower device 100 closer to the ground.

Figure 5:
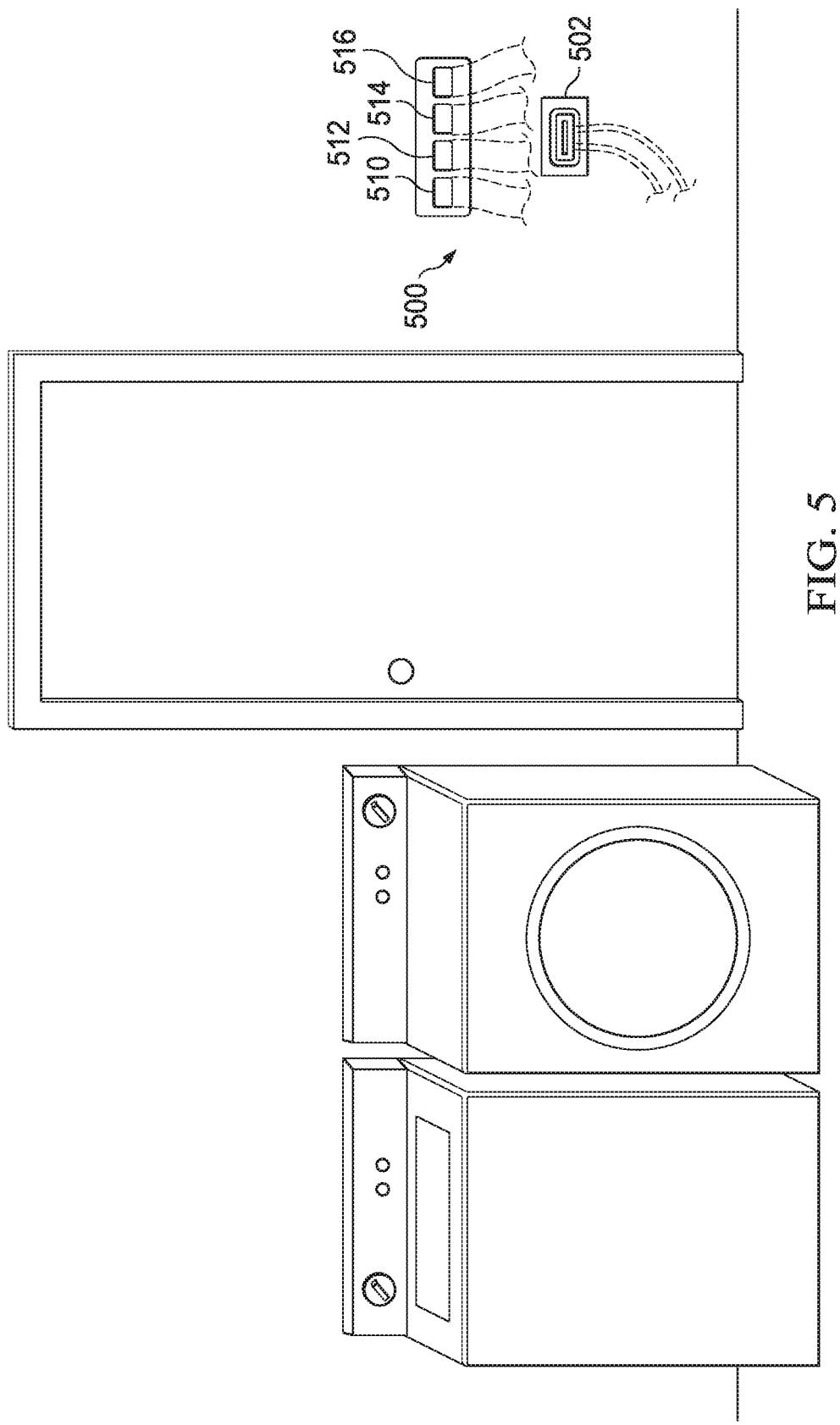
FIG. 5 is a block diagram of a docking station 500 for device 100 according to one embodiment of the present disclosure.

FIG. 5 is a block diagram of a docking station 500 for device 100 according to one embodiment of the present disclosure. Docking station 500 interfaces with charging ports 300 and electrical ports 302. Docking station 500 comprises a food recharger port 510, a water recharger port 512, a medicine recharger port 514, a waste removal port 516 and an electrical recharging interface 502.

Food recharger port 510 comprises a suitable system to couple and decouple to food port 310 in order to refill food bin 322 via food port 310. For example, food recharger port 510 and food port 310 may comprise a pair of generally hollow cylinders where one cylinder is slightly larger than the other cylinder to allow the smaller cylinder to enter into the larger cylinder to create a connection where solid and/or liquid food can pass through from food recharger port 510 to food port 310 into food bin 322.

Water recharger port 512 comprises a suitable system to couple and decouple to water port 312 in order to refill water bin 320. For example, water recharger port 512 and water port 312 may operate similarly to ports 510 and 310.

Medicine recharger port 514 comprises a suitable system to couple and decouple to medicine port 314 in order to refill medicine bin 324. For example, medicine recharger port 514 and medicine port 314 may operate similarly to ports 510 and 310.

Waste removal port 516 comprises a suitable system to couple and decouple to waste port 316 in order to allow the emptying of waste bin 326. For example, waste bin 326 may become partially or completely filled with solid and/or liquid waste as a result of the cleaning of tray 118. Waste removal port 516 and waste port 316 may operate similarly to ports 510 and 310.

Electrical recharging interface 502 comprises a suitable electrical system for recharging battery 340 via port 302. For example, interface 502 and port 302 may comprise a suitable male/female electrical connection system.

As illustrated in FIG. 5, docking station 500 may be located at a suitable location, such as a laundry room or outdoor location, for recharging and refilling device 100. In one embodiment, docking station 500 is located outdoors and uses equipment suitable for outdoor and/or harsh environment use. Device 100 may automatically detect that one or more of bins 320, 322, 324 and 326 need refilling or emptying and return to docking station 500 and/or notify the caregiver that one or more of bins 320, 322, 324 and 326 need refilling, or that battery 340 needs recharging. Alternatively, the caregiver may remotely command device 100 to return to docking station 500 and/or device 100 may return to docking station 500 on a predetermined schedule or in response to other inputs. Docking station 500 itself may also be operable to generate a notification to the caregiver that the docking station 500 requires refilling.

In operation, device 100 may be used by an animal caregiver to assist with the care of one or more animals, regardless of whether the caregiver is physically located near the animals or is physically distant. Device 100 may be directly controlled by the caregiver, such as via a remote control or via a network connection, such as via an application on a computer, smartphone, tablet or other electronic computing device, that communicates with device 100 over a global computer network, such as the Internet. In addition, device 100 may be pre-programmed to perform various activities independently. For example, device 100 may provide food, water and/or medicine on tray 118 at predetermined times. Device 100 may also be controlled via a combination of independent programming and remote control.

Initially, or after one or more uses of device 100, device 100 is filled and charged, or refilled and recharged, at docking station 500. For example, device 100 may be controlled by a remote control by a human user or may be capable of automatically finding docking station 500, such by GPS location or a beacon of a suitable type that device 100 may navigate to. In one embodiment, device 100 rolls to docking station 500 and reverses into docking station 500. Rear wheels 108 then articulate to allow device 100 to lower or raise itself and couple ports 300 and 302 with docking station 500.

The animal caregiver may interact with the animal using display 116 and camera 112. Camera 112 allows the caregiver to see the animal, and may provide a pan, tilt and/or zoom functionality to improve viewing of the animal from a remote location, such as over the Internet. Display 116 allows the animal to see an image, such as the caregiver. Display 116 comprises any suitable display system for video and audio and is capable of receiving video and audio via wireless system 110. The audio capabilities of display 116 allow the animal to both see and hear the caregiver, and allow the caregiver to hear the animal. For example, the caregiver could program device 100 to generate familiar sounds, such as a normal pre-sleep ritual, associated with the caregiver at a certain time, such as when the animal is sleeping. In general, device 100 may play pre-recorded audio and/or video messages at pre-determined times, in response to predetermined situations and/or as commanded remotely by the caregiver, such as via an application on a smartphone used by the caregiver. In addition, toy 114 allows the caregiver to play with the animal. For another example, a veterinarian may use camera 112 to evaluate the medical condition of an animal under the care of device 100.

As device 100 is mobile, device 100 can move around with the animal. In one embodiment, wireless system 110 generates a signal usable as an electronic fence system. Electronic fences are commonly used to keep an animal, such as a dog, within a predefined area without the use of physical barriers. For example, the electronic fence may be linked to a shock collar that indicates that the dog is not allowed to go beyond a certain point. Such an electronic fence system, when incorporated into device 100, allows device 100 to walk an animal. For example, an animal that has been trained that the animal can only go a certain distance, such as 50 feet, away from device 100 by the electronic fence, allows device 100 to walk the animal. More specifically, since the animal knows that it must remain within a certain distance from device 100, or be subject to appropriate corrective measure, such as an audible signal or an electronic shock from a shock collar, device 100 could, for example, move down a sidewalk along a predetermined route, or under the remote control of a care giver, and walk an animal even though the care giver is not physically present. In one embodiment, the electronic fence collar worn by the animal contains a water immersion detection capability to detect if the animal has entered or fallen into a body of water, such as a swimming pool, lake or pond. In this embodiment, the collar may alert device 100 that the animal has entered a body of water and the device 100 may generate an alert, such as to the remote care giver or an emergency response group, or take other predetermined actions in response thereto.

Device 100 may use a GPS or other location device associated with device 100 and/or the animal being cared for to provide location information of the animal and/or device 100 to the animal caregiver. The location information may be used by device 100 to generate an alert to the caregiver and/or other people based on one or more predetermined conditions. For example, an alert could be generated if the animal goes beyond a certain distance from device 100. In one embodiment, device 100 communicates with a device that tracks an animal's vital signs and responds appropriately in the event of a medical emergency. For example, if it is known that an animal has a medical condition that requires medicine only under certain circumstances, device 100 could provide such medicine via tray 118 or payload 122 when the medical condition is detected by the vital signs monitoring device, such as in response to low blood sugar, elevated blood pressure or elevated heart rate.

In addition, device 100 may include special programming to automatically handle emergency situations. For example, device 100 may be capable of communicating with a smoke and fire detection system in a house, and use the electronic fence functionality to bring a house pet outside in the event of a fire, such as by decreasing the distance of the electronic fence to keep the animal close to device 100 until device 100 and the animal have reached a safe or predetermined location. In one embodiment, device 100 may itself be equipped with a carbon monoxide detector, smoke detector, fire detector and/or other sensors to detect toxic fumes, smoke, fire or other hazards. For example, device 100 may include a glass break sensor along with programming to know that device 100 and an animal under the care of device 100 are alone in a structure, and that a glass break represents a potential intruder. For another example, device 100 may include programming to generate an alert to an emergency service, such as a fire department, that includes images, description and count of the animals under the care of device 100. Such an alert may be sent when device 100 detects a hazardous situation, such as a fire, so that emergency responders are aware of the number and identity of animals in a structure. In addition, such an alert may include medical information, such as drug allergies, handicaps or pregnancy, of animals under care of device 100 to assist medical personnel in an emergency. Further, such an alert may also include the planned emergency evacuation location that device 100 will lead animals to in the event of an emergency to assist first responders in locating the animals. In general, device 100 may be programmed to communicate current and/or historical data associated with one or more sensors associated with device 100 to the caregiver and/or may be commanded by the caregiver to provide such data.

Tray 118 allows device 100 to feed, water and provide medicine to animal. In one embodiment, when an animal is to be fed, such as device 100 being preprogrammed with feeding times, determining feeding is necessary according to predetermined criteria or is commanded to feed the animal by the caregiver, device 100 fills tray 118 with food, water and medicine (if needed). For example, food, water and medicine from bins 320, 322 and 324 may be respectively deposited in tray portions 200, 202 and 204. Tray 118 may use portions 200, 202 and/or 204 for uses other than food, water and medicine. For example, portion 200 may be used as a cat litter box instead of providing food.

Device 100 then lowers itself so that the bottom of tray 118 is generally in contact with the ground and releases tray 118. For example, device 100 may use rear wheels 108 to pivot the front of device 100 generally downward and then reverse, while allowing tray 118 to slide out. Alternatively, after the bottom of tray 118 is generally in contact with the ground, device 100 may release tray 118 and raise itself back up to a normal operating height and leave tray 118 on the ground. In general, any suitable system for releasing and recovering tray 118 may be used by device 100.

After the animal has finished eating and drinking, device 100 retrieves and cleans tray 118. For example, device 100 may lower itself over tray 118, reattach tray 118 to device 100, and raise itself back to a normal operating height. Alternatively, device 100 may slide tray 118 back into device 100. Device 100 then cleans tray 118 using cleaning nozzle 330 and suction nozzle 332. In one embodiment, device 100 may also use cleaning nozzle 330 and suction nozzle 332 to clean up detected debris, such as animal excrement or soil from a flowerpot knocked over by an animal. For example, caregiver could notice such debris via camera 112 and remotely control device 100 to leave tray 118 at a suitable location to allow use of nozzles 330 and 332 to clean up such debris. Alternatively or in addition, device 100 may automatically detect such debris and perform an appropriate cleaning operation. In addition, in one embodiment, device 100 may include a heater and/or air blower device associated with nozzles 330 and/or 332, to dry the area cleaned by nozzles 330 and 332. Further, in another alternative embodiment, scent emitter 130 may include the additional ability to emit a scent designed to be pleasing to humans, such as a scent similar an air freshener that is emitted on or near a recently cleaned area to lessen offensive odors that may remain after the cleaning process.

Device 100 may also communicate with a home automation system that allows device 100 to open and close doors in a structure. For example, device 100 could wirelessly lock and unlock doors equipped with appropriate devices and push open doors for the animal at appropriate times, such as to allow the animal outside to play at certain times. In addition, device 100 may use such control over doors to control which areas of a structure that an animal is allowed to enter or prohibited from entering. Device 100 may also use such a home automation system to control environmental conditions, such as a heater or air conditioner. In addition, in one embodiment, device 100 may also communicate with a security system to allow an animal to move about the house without activating the alarm. For example, many security systems use motion detectors to provide security for a structure, however, such motion detectors often generate false alarms when an animal triggers the motion detector. Device 100 may avoid such false alarms by deactivating the motion detector when location information associated with an animal indicates that an animal is near a motion detector controlled area. For another example, device 100 may detect than a dog has spent a significant amount of time in front of a door that the dog uses when the dog needs to relieve itself. Upon detecting that the dog has been in front of the door for an appropriate period of time, device 100 could unlock and/or open the door to let the dog out, and deactivate the alarm system on that door to prevent a false alarm, while still allowing the alarm system to be used with an animal in the house.

Device 100 may also record the location of itself and/or the animal and provide such information to the caregiver. For example, device 100 may use the GPS device to provide a map of movements over a period of time to the caregiver via a remote data connection.

Device 100 may also include programming to detect if the animal has remained stationary for an abnormally long period of time, such as by using GPS information communicated from a collar worn by the animal to device 100. For example, if a normally active animal has not moved for several hours, this may indicate a medical problem or that the animal is deceased. The programming may take any suitable action in response thereto, such as generating an alert to the caregiver or an emergency response group, or by providing medicine to the animal, such as via arm 120.

The animal care device 100 may be preprogrammed with a "route" to walk an animal or a human can control the animal care device 100 remotely to move it along a path walking the animal either with a tethered leash or using the wireless "geofence" which uses the smart collar 608 to determine one or more of the animals current position, its direction of travel, its distance from the animal care device 100, its proximity to known hazards (lakes, pools, streets, highways) and the animal care device 100 administers to the animal via the smart collar 608 or a separate shock collar, a corrective shock or other type of corrective signal (audio/video) to cause the animal cease its movement in a specific direction, cause it to move, cause it to maintain a certain distance within a predetermined perimeter of the animal care device 100 or affect the animals movement or behavior in any way.

Figure 6:
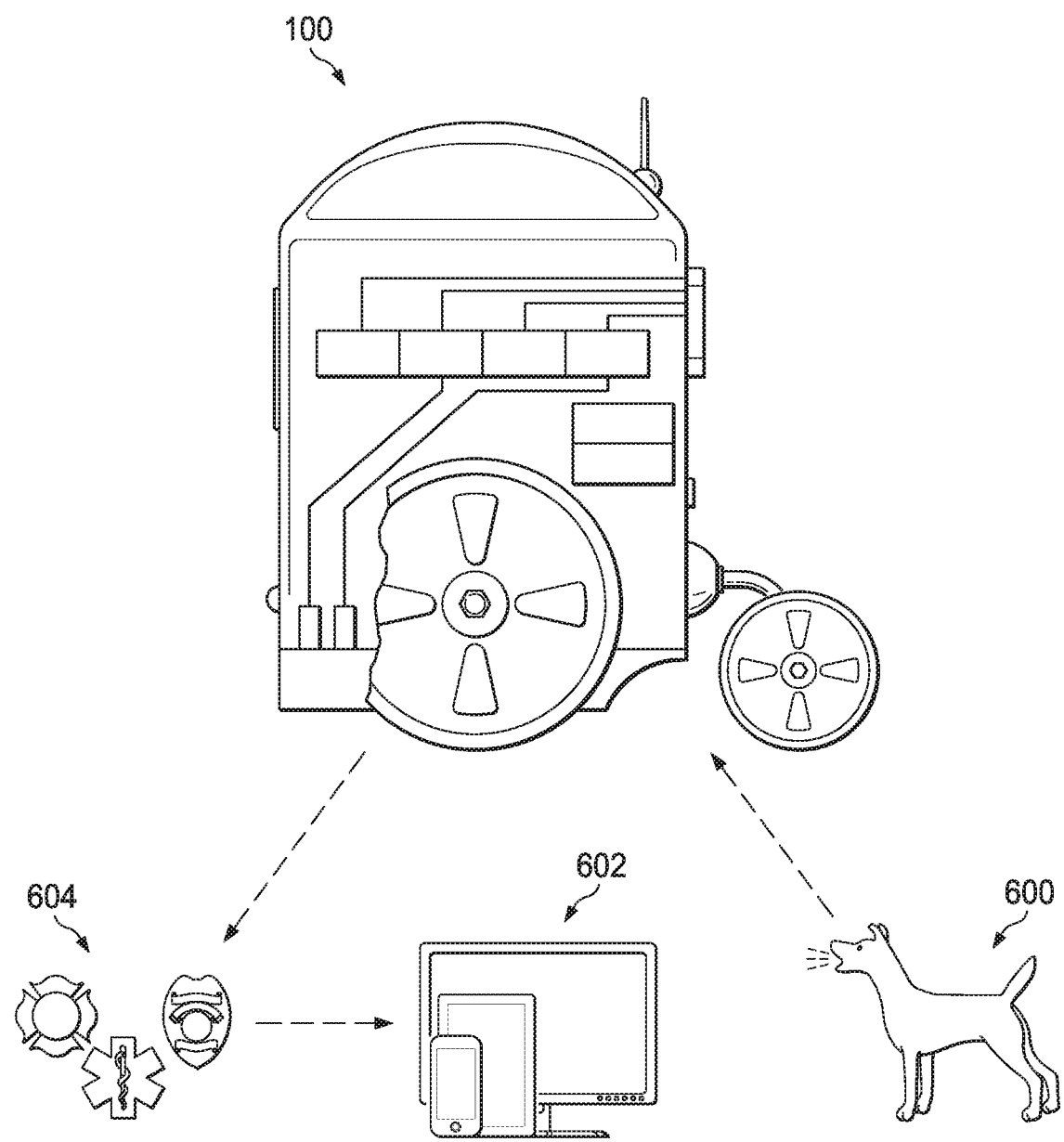
FIGS. 6-8 are diagrams illustrating information flows in exemplary embodiments of an animal care device 100 according to the teachings of the present disclosure.
Figure 7:
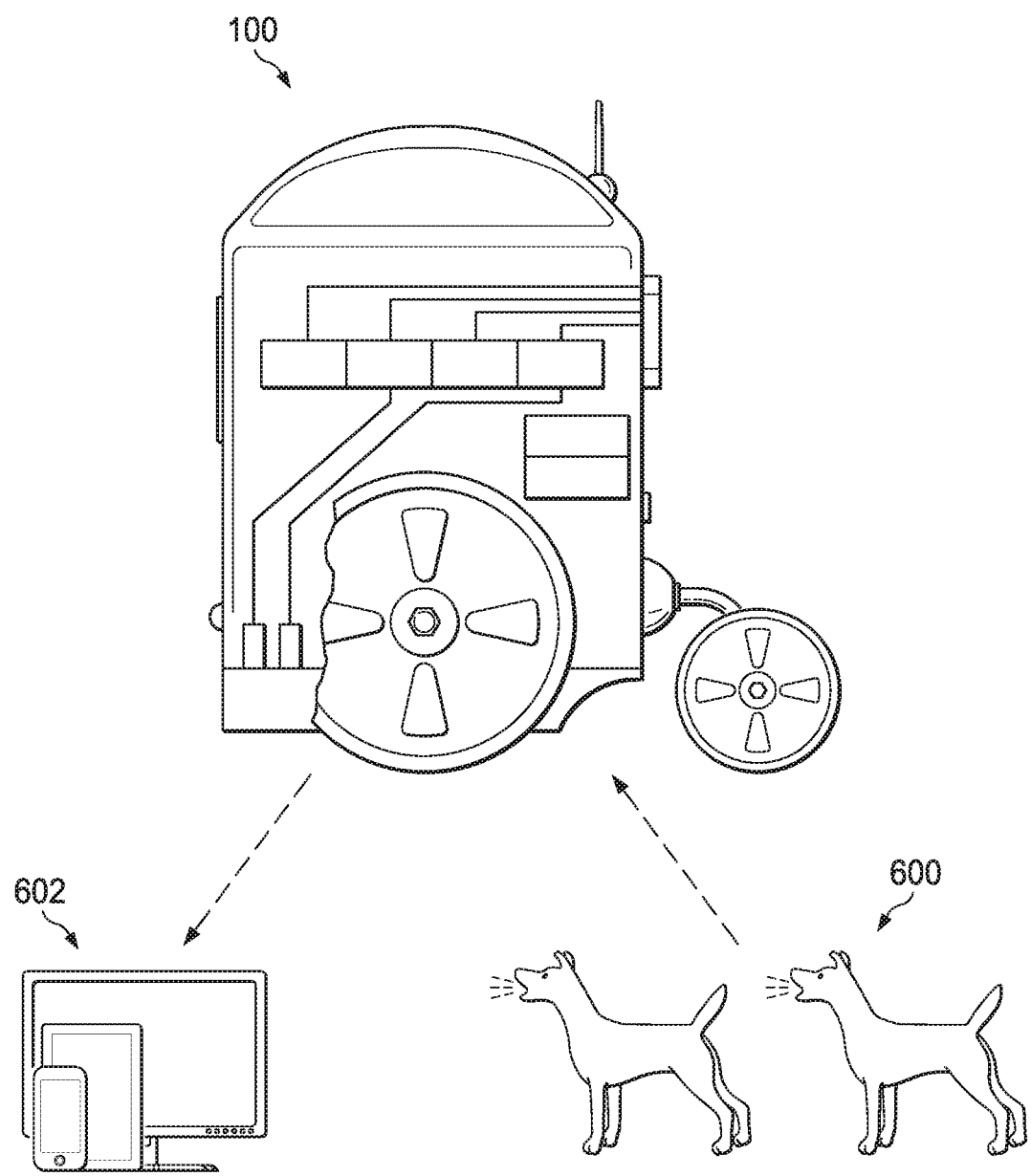
Figure 8:
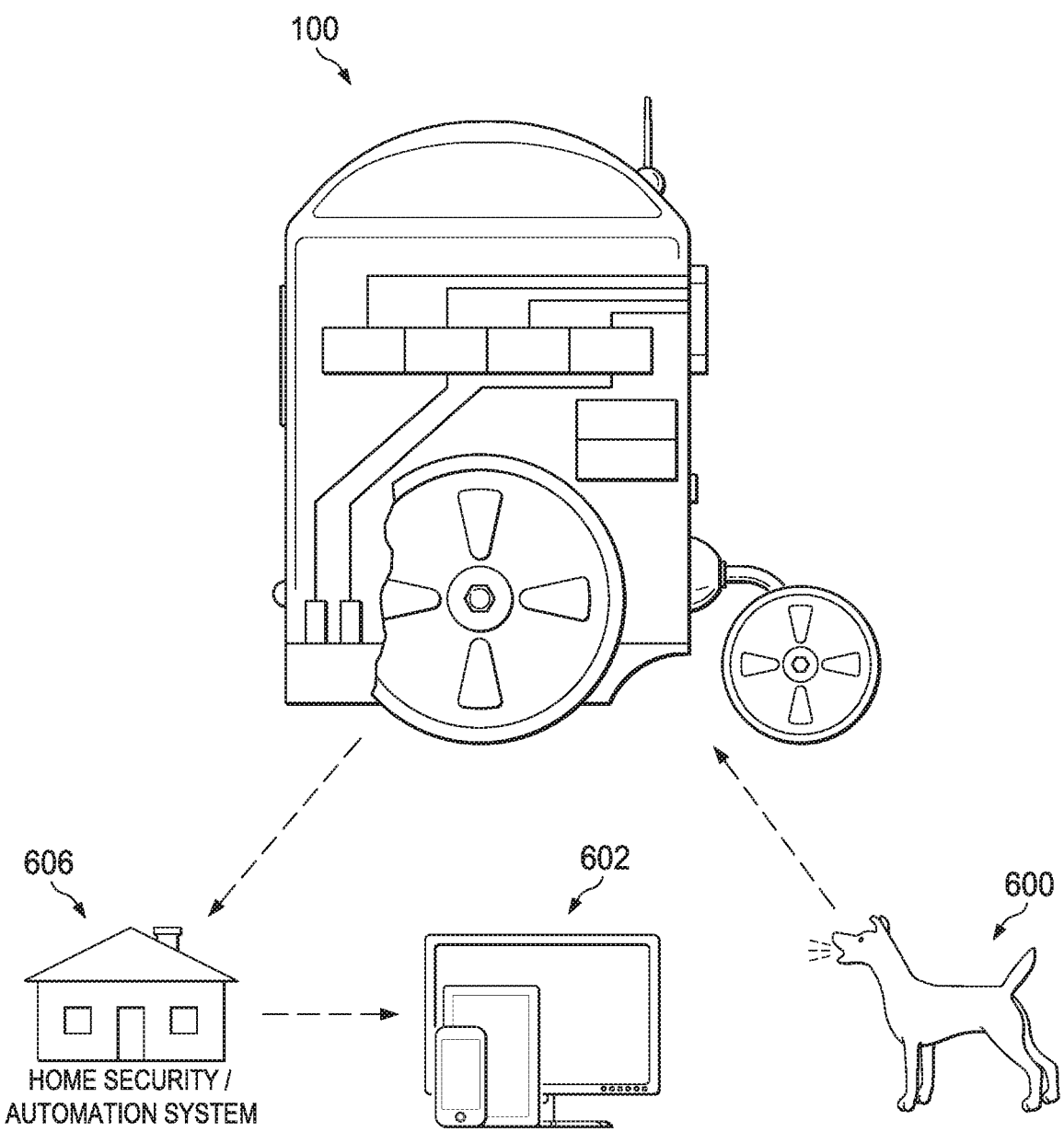

FIGS. 6-8 are diagrams illustrating information flows in exemplary embodiments of an animal care device 100 according to the teachings of the present disclosure and are described in turn. The animal care device 100 is equipped with a bark recognition sensor logic capable of "learning" unique barks or sounds of distress associated with individual animals 600 and differentiating between the barks or distress sounds to determine which individual animal 600 is making the sound, if multiple animals are present and notifying the owner of one-time or continuous dog barking and identifying the dog that is barking. The animal care device 100 is capable of interfacing with and activating personnel or home security system 606 (alarm, directing security cameras toward the sound of the barking, etc.) if the barking exceeds certain parameters (example, constant barking for more than 30 minutes, etc.) and also notifies the owner via a user computing device 602, e.g., cell phone, tablet, or computer, or notify a third person or agency 604. The animal care device 100 may take action based on the bark i.e., arming the security system 606, and/or opening a door to allow egress or access to the outside or inside of a building or room. Having the animal care device 100 begin recording when a bark is detected, or alert the owner of a possible threat and allow the owner to view the location via the audio video features of the animal care device 100.

The animal care device 100 may operate in a bark suppression mode to dissuade and prevent an animal 600 from making certain noises (i.e., bark suppression system consisting of an audible noise or image or a preset message from the owner or a noise emitter to calm a horse when the animal care application recognizes noises or sounds associated with the animal being "spooked"). The system can be activated by a preset sensing system or by a library of sounds recorded and loaded onto the system with a unique suppression or calming response programmed for each noise in the library.

Figure 9A:
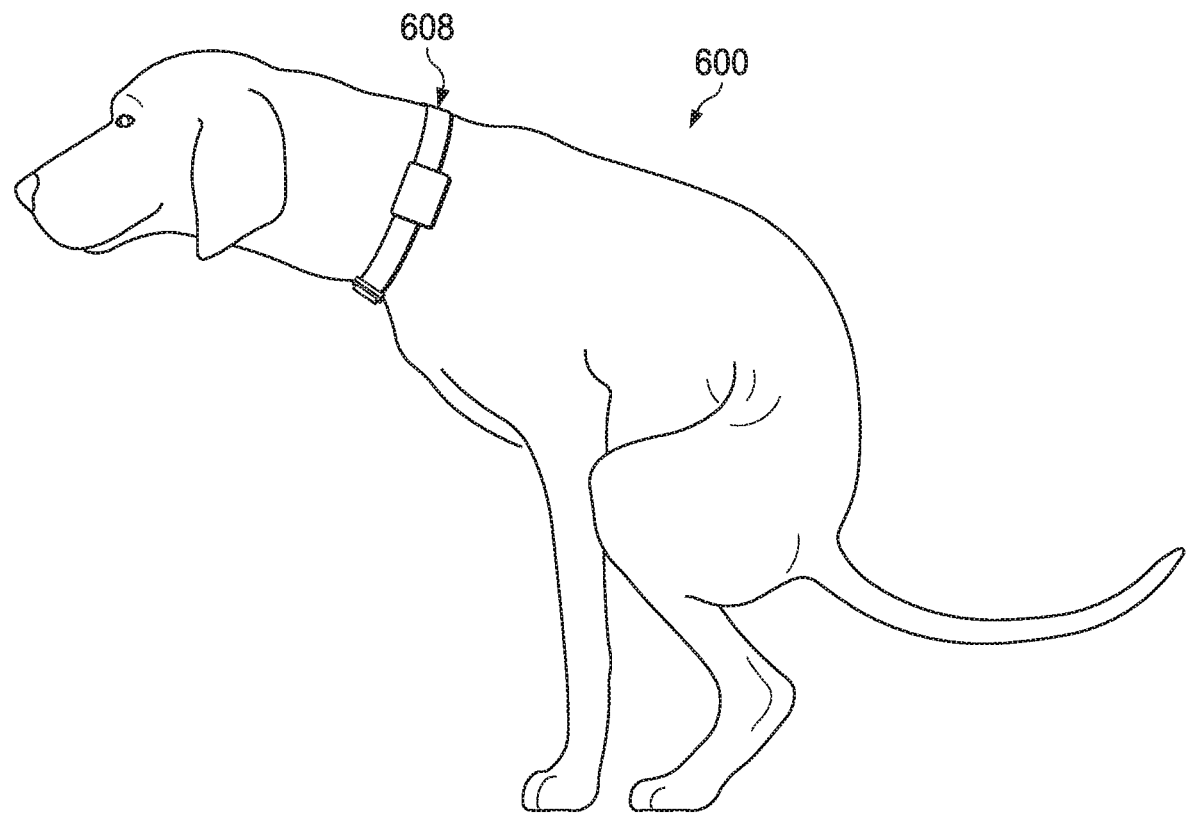
FIGS. 9A and 9B are illustrations of an exemplary embodiment of a smart collar 608 and a dog wearing the smart collar 608 according to the teachings of the present disclosure.
Figure 9B:
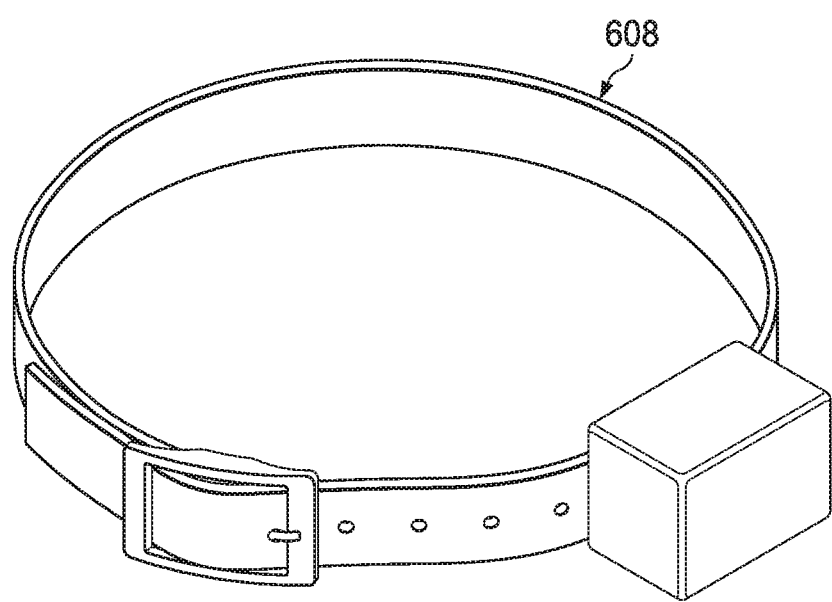
Figure 10A:
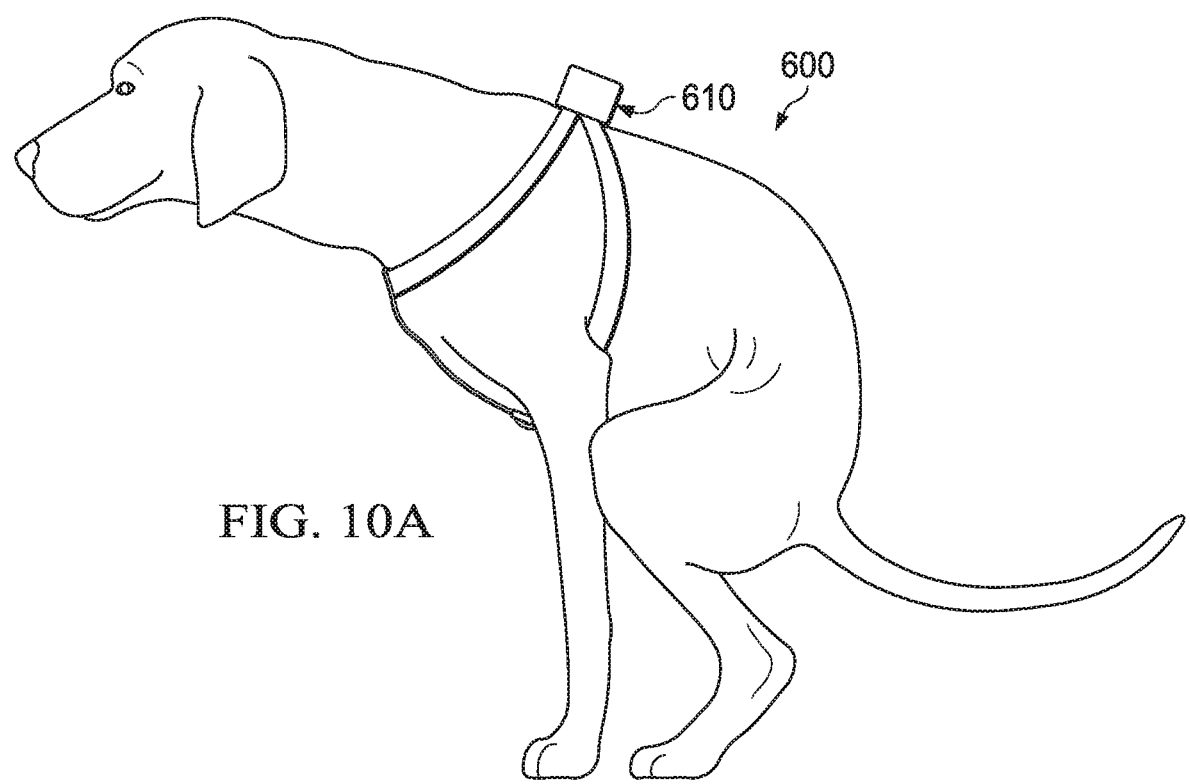
FIGS. 10A and 10B are illustrations of an exemplary embodiment of a smart collar and a dog wearing the smart collar 608 according to the teachings of the present disclosure.
Figure 10B:
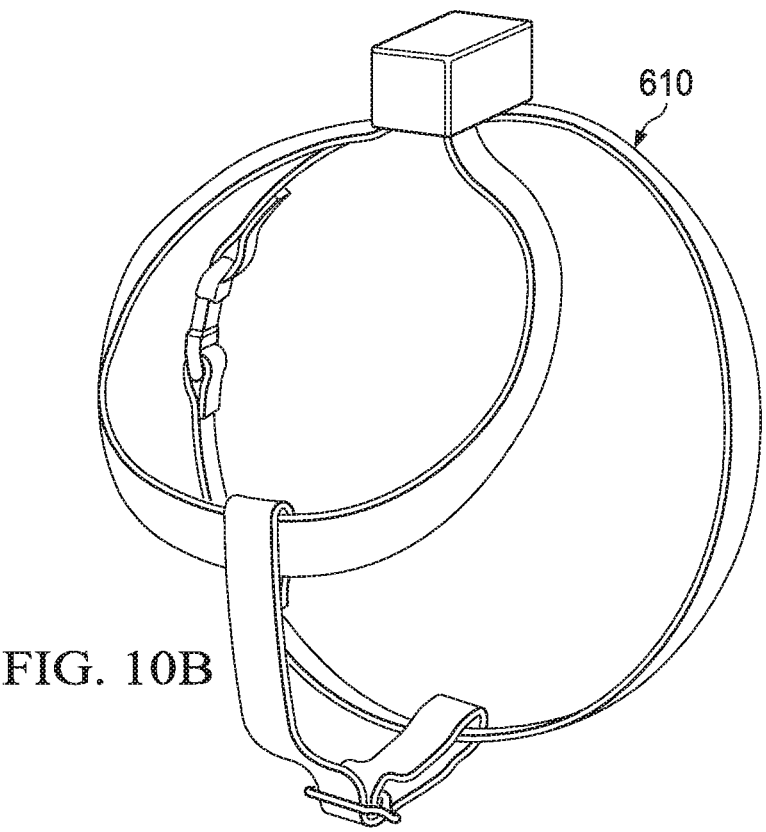
Figure 11:
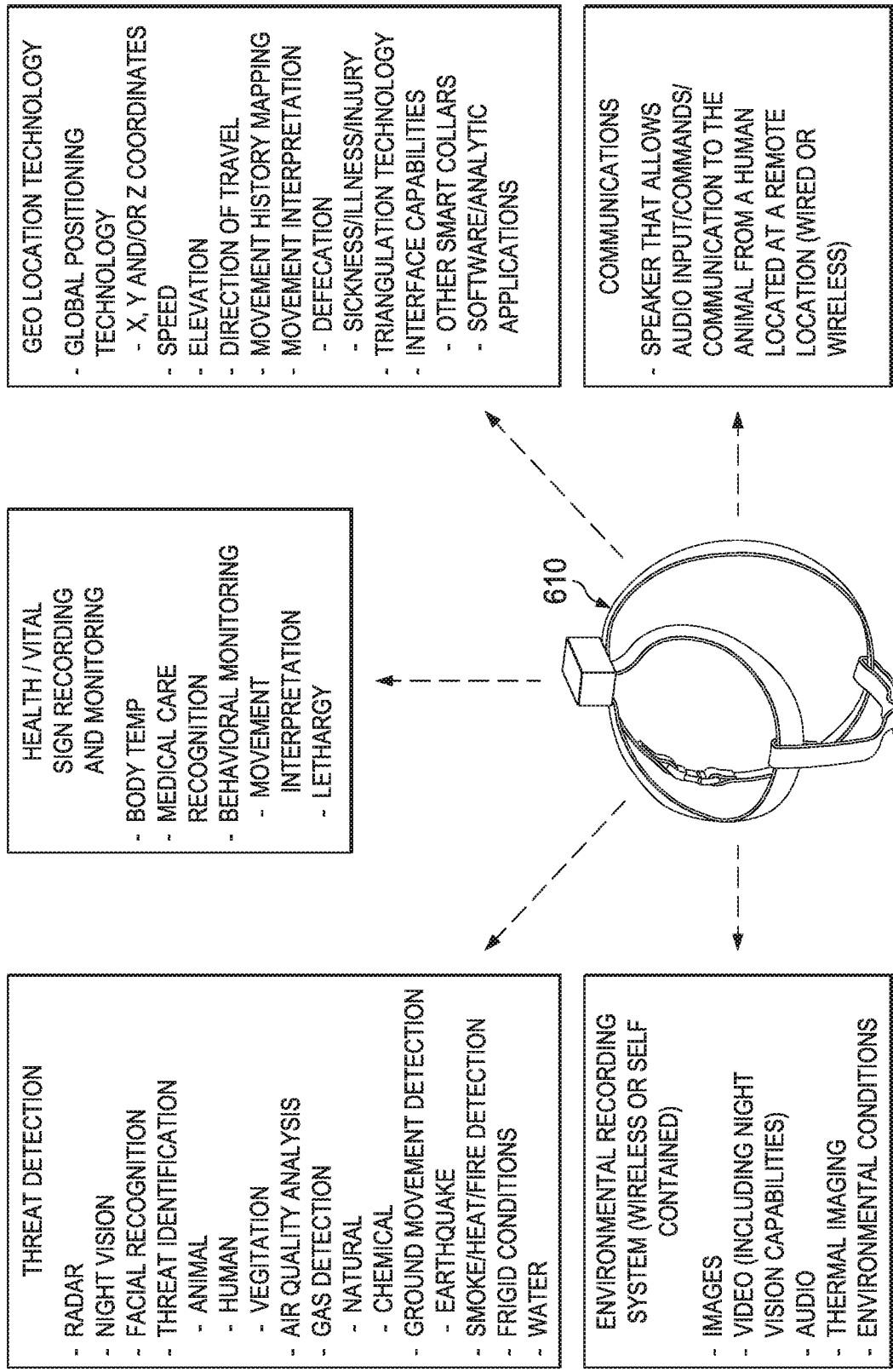
FIG. 11 is a diagram illustrating a variety of applications for a smart collar 608 according to the teachings of the present disclosure.

FIGS. 9A and 9B are illustrations of an exemplary embodiment of a smart collar 608 and a dog 600 wearing the smart collar 608 according to the teachings of the present disclosure. FIGS. 10A and 10B are illustrations of an exemplary embodiment of a smart harness and a dog wearing the smart harness 610 according to the teachings of the present disclosure. For purposes of this disclosure, the smart collar 608 and smart harness 610 are equivalent in functionality in the animal care technology described herein. FIG. 11 is a diagram illustrating a variety of applications for a smart collar 608 according to the teachings of the present disclosure.

Figure 12:
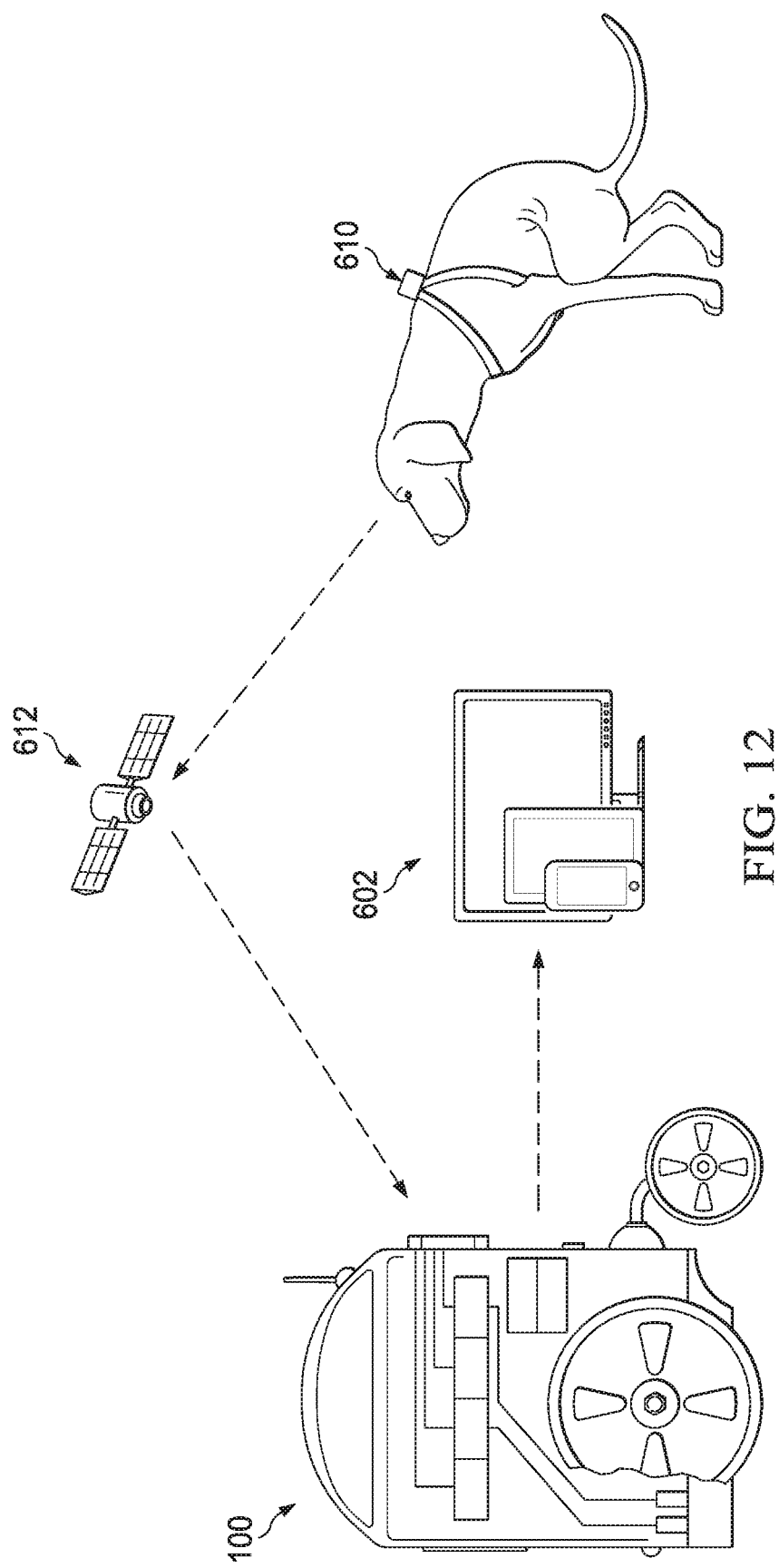
FIGS. 12 and 13 are diagrams illustrating information flows in exemplary embodiments of an animal care device 100 operating cooperatively with a smart collar 608 according to the teachings of the present disclosure.
Figure 13:
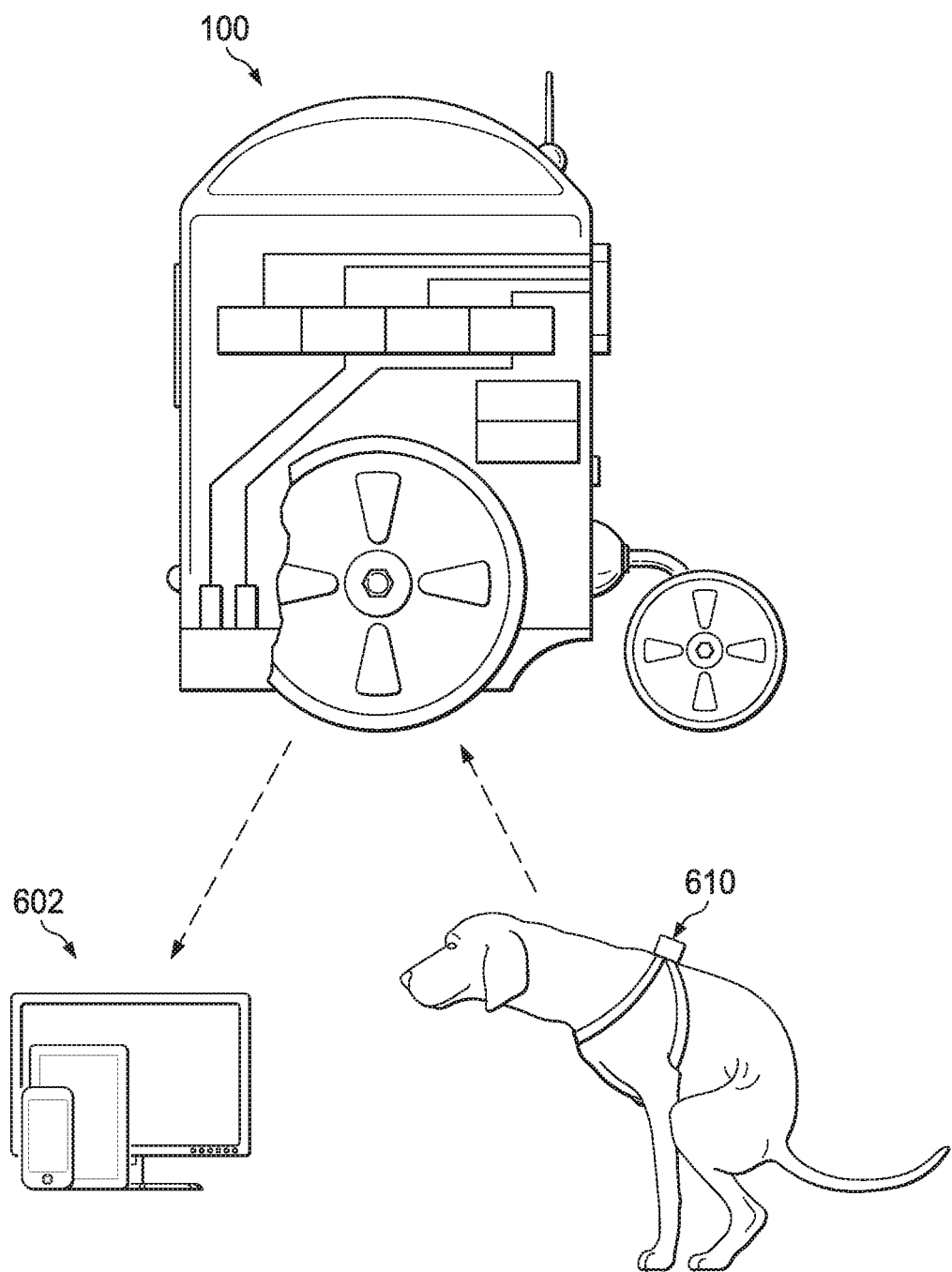

FIGS. 12 and 13 are diagrams illustrating information flows in exemplary embodiments of an animal care device 100 operating cooperatively with a smart collar according to the teachings of the present disclosure. The smart collar 608 will detect geographical coordinates using GPS (global positioning system) 612 and other suitable methods, and can be both preprogrammed with known animal characteristics from a library of known animal movements or capable of learning and storing the movement a particular animal movements and associating those movements with a certain activity the animal is performing (i.e., eating, jumping on the couch, defecating, chasing another animal, sleeping, chewing on something, etc.) and based on the activity the animal care device 100 will respond with a preprogrammed response based on the activity the animal 600 is involved in (example jumping on the couch when it is not supposed to) or a combination of learned traits combined with GPS (global positioning system) location (i.e., the animal is in the living room, on the couch, exhibiting a movement consistent with eating, the animal care device 100 is programmed to assume it is chewing on a pillow and responds with an audio, audio/video, alarm or collar shock or other response designed to correct the animal 600 and stop the behavior. It may also alert the owner and allow the owner to initiate a response remotely or speak to the animal via video or audio to correct the action.

In the excrement cleanup application, the smart collar 608 will interpret movements related to the animal defecating and transmit the location (e.g., absolute such as latitude and longitude or relative to one or more landmarks in the yard or residence) of probable defecation ("LPD") to the animal care device 100 which will then, automatically or after manual initiation by a human, perform a cleaning function by going to those locations of high probability, cleaning the feces by scoop, vacuum, pincher, shovel or other method, storing the feces in the animal care device 100 and allowing the feces to be expelled either automatically by the animal care unit and preprogrammed time and location or manually by the owner. The animal care device 100 may also be capable of packaging the feces in a bag, membrane or covering for easy disposal. In another embodiment, an on-board incinerator my burn the feces or use chemicals or other methods to destroy the feces. Alternatively, the animal care device 100 may alert the owner who may manually initiate the process.

The smart collar 608 and animal care device 100 may cooperate for additional functions. For example, the smart collar 608 and/or animal care device 100 may be capable of taking an animal's external body temperature via thermal imaging or any other heat sensing technology, or via a probe extended from the animal care device 100 to make contact with the animal. The system would notify a remote entity or third party (owner, veterinarian, etc.) if the animal's body temperature is out of a preset range and prompt attention is required.

The animal care device 100 may be further equipped with a wirelessly-connected interface with an existing or designed weather reporting or forecasting application to allow the animal care device to determine or restrict the activity of the animal based on the current weather or the forecast (i.e., don't let the dog out in the yard in a lighting storm, or turn up the heat if cold weather is forecasted). A pre-programmed animal "care" routine based on the time of day, day of week, actions of the animal, weather or any other factor may direct the animal care device 100 to initiate a sequence of actions based on a particular time or circumstance so that the animal is away from possible harm and is in a safe and comfortable environment.

A recording system may be mounted on-board the animal care device 100 that can record and store external images, video or environmental conditions continuously, or on a pre-configured time schedule or based on some external event. These images may be transmitted to one or more destinations for viewing online by the owner or other authorized personnel. The images may further be analyzed for threat detection.

A self-contained medical diagnostic program may be on-board the animal care device 100 that senses, via the smart collar 608 or other input, that the animal's behavior or vital signs are consistent with some type of illness or distress, and administers care and/or medicine to address behavior or vital signs associated with illness or distress. For example, if the animal care device 100 determines the animal is making body movements consistent with scratching, it may administer tick prevention medicine. If the animal care device 100 determines that the animal is dragging its hind quarters across the floor, it may administer worming medicine. The animal care device 100 response may also be triggered by medical events recognized by the smart collar and an on-board medical library that matches the movements of the animal to the probability of certain injuries, sicknesses or illnesses.

An on-board stool examination component incorporated within or attached to the animal care device 100 that is locates and gathers an animal's stool/feces automatically (feces cleanup technology) or a sample is loaded manually, and then examined and evaluated for signs of disease, parasites (worms. etc.) or other abnormalities, and alerts a person (owner, caretaker, veterinarian) of the results of the stool evaluation.

An on-board "radar" or "threat detection" system or animal "facial recognition" component(s) incorporated within or attached to the animal care device 100 that detects other animals in the proximity of the animal associated with the animal care device 100 and alerts a person of the nearby animal or potential threat. The system may have an "intelligent" or artificial intelligence component that interprets the movements, size, mannerisms, geo-location (does the possible list of animals detected have a population in the area?), etc. For example, if the animal care device 100 detects a bear and the geo-coordinates indicate the associated animal is in Alaska, the system would identify the possible threat specifically as a Brown Bear. If the animal care device detects a larger upright animal and the geo location determines the associated animal is in Australia, the threat may be identified as a Kangaroo).

The animal care device 100 and/or the smart collar 608 may have a camera/video capture component which interfaces with a facial recognition database. The camera/video component can evaluate images of a person or persons near the device or the associated animal and determine if the person is known (owner, caregiver, veterinarian, etc.) or unknown or if the person is a known potential threat. If the person is not a known or "allowed" person the animal care unit may control the movement of the associated animal to keep the animal away from the person for the protection of the animal or the unknown person. The animal care device 100 may also issue an audible or visual warning or message, or if the person is known, it may issue a message (e.g., "Hello Joe, Rover has not eaten yet today but has gone to the bathroom within the last 10 minutes.")

The smart collar 608 facial recognition component may be interfaced, either directly or via the animal care device 100, to a system that notifies a remote entity, such as a third person or agency if an unauthorized individual is detected in a certain area (i.e., intruder in house), the person is in need (i.e., missing Alzheimer's patient) or a threat to people in the area (sex offender detected at a playground near kids).

The animal care device 100 may have an audible or visual warning that locates and contacts the animal owner (either via a wireless communication, text, cellphone etc.) or identifies the owner in proximity to the animal care device 100 (via the facial recognition or other identification technology) and reminds the owner that attention is needed by the associated animal ("Joe, Rover needs his allergy shot within the next 2 days" or "Joe, please remember that Rover has a doctor's appointment on Tuesday at 1:00 pm").

The smart collar with the on-board camera/video capture device may transmit images to the associated animal care device 100 or a separate database for comparison with known persons who may be missing, wanted by authorities, or in need of assistance. It may also use facial recognition technology to identity individual animals and identify them as belonging at the location or missing from another location.

The smart collar 608 may be equipped with a hazardous substance or gas detection component that identifies potential air quality threats to the animal 600, other animals or persons in the area. Upon detecting such hazards in the environment, it may transmit information to a home security system, or the animal care giver or other persons either directly or via the animal care device 100.

The smart collar 608 may be equipped with a wireless audio component that interfaces with an external application to allow a person to give audible instructions or reassurances to the animal from a distance. The user interface may be an application executing on a mobile device, such as a mobile phone, for example.

Figure 14:
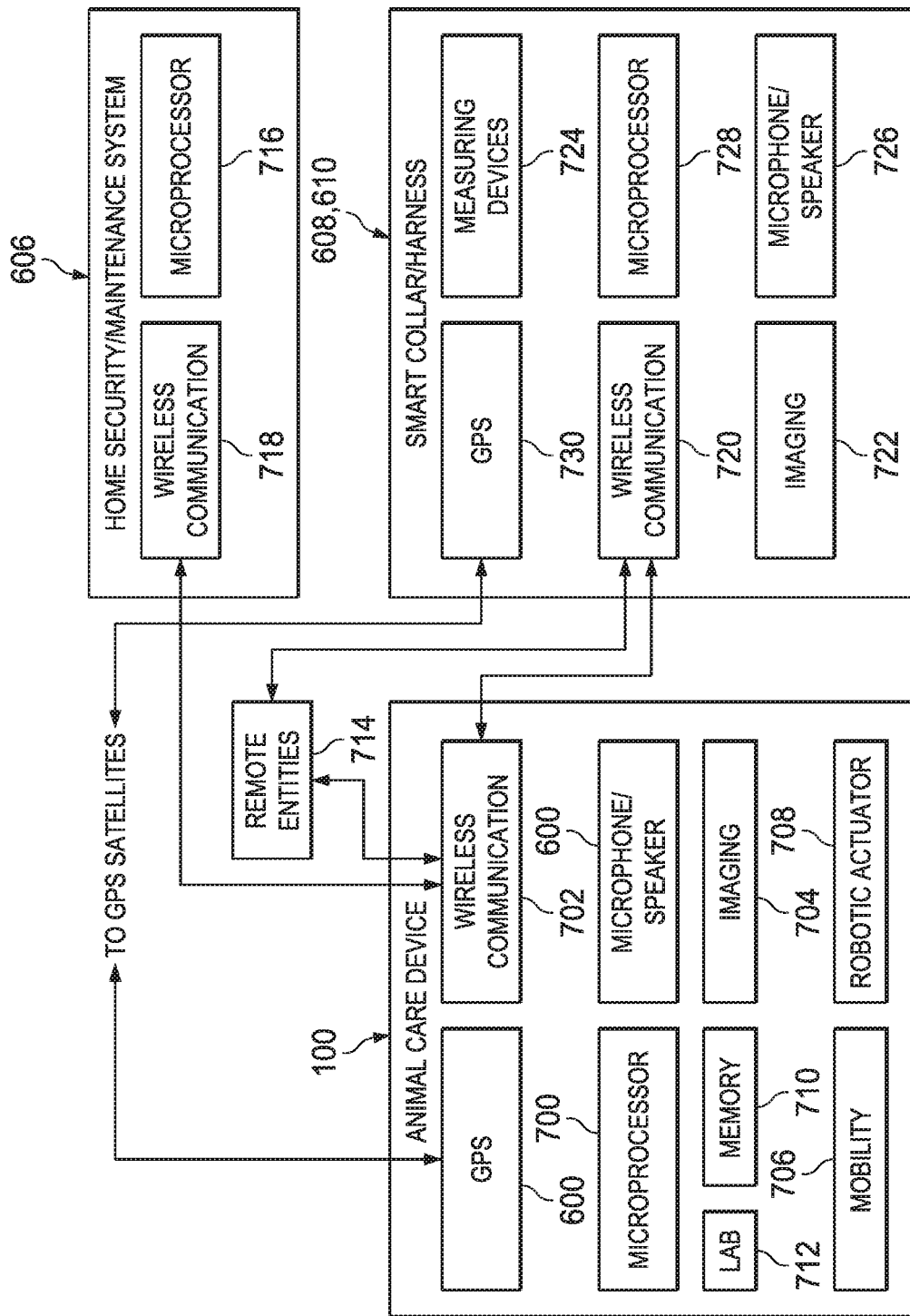
FIG. 14 is a simplified block diagram of an exemplary embodiment of an animal care device 100 in operation with a smart collar 608/smart harness 610 according to the teachings of the present disclosure.

FIG. 14 is a simplified block diagram of an exemplary embodiment of an animal care device 100 in operation with a smart collar 608 according to the teachings of the present disclosure. The animal care device 100 includes a microprocessor 700 in communication with a wireless communication system 702 that enables data to be transmitted to and from the animal care device 100. The term "wireless communication" herein is used broadly to refer to any communication channel, now known or to be developed, that can be used to transmit and receive data signals without any physical or tangible medium such as a copper line or fiber optic cable. However, it is contemplated that physical transmission media may be employed along at least some portion of the network path from the origination point (e.g., animal care device 100) to the termination point of the data (e.g., remote entity 714).

The animal care device 100 further includes an imaging system 704 operable to take still photographs and/or video images. The animal care device 100 further includes a mobility portion 706 that enable it to move about its environment according to instructions from the microprocessor 700. An additional equipment is a robotic actuator 708, in the form of, for example, scoop, vacuum, pincher, shovel or combination thereof that is operable to pick up, sample, and dispose of items, such as the animal's feces. The microprocessor 700 is also operable to access a memory 710 for executable program code and to store and read data. The microprocessor 700 is also able to communicate with an automated laboratory 712 to receive laboratory report and analysis generated by the laboratory. The wireless communication device 702 on-board the animal care device 100 may further enable it to communicate with a remote entity 714, such as home security monitoring service, a computing device of the owner, or a separate security/home maintenance system 606. In addition, the animal care device 100 may be in communication and/or controlled by a home security/maintenance system. In particular, the microprocessor on-board the animal care device 100 may be optional, and the animal care device 100 may be instead under the control of a microprocessor 716 of the home security/maintenance system via its wireless or wired communication system 718. In addition, the smart collar 608/harness 610 includes a wireless communication system 720 for communications with the animal care device 100 (or in the alternative, with the home security/maintenance system). The smart collar 608 also includes an imaging system 722 for capturing still photographs and video images, a measuring device 724 capable of measuring or sampling a variety of substances and/or states (liquid, gas, body temperature, pulse rate, etc.), and a microphone 726 for receiving audio data, and a speaker 726 for generating audio signals. The smart collar 608 may include an on-board microprocessor 728 and a GPS system 730 for determining a geo-location of the animal wearing the smart collar 608.

Figure 15:
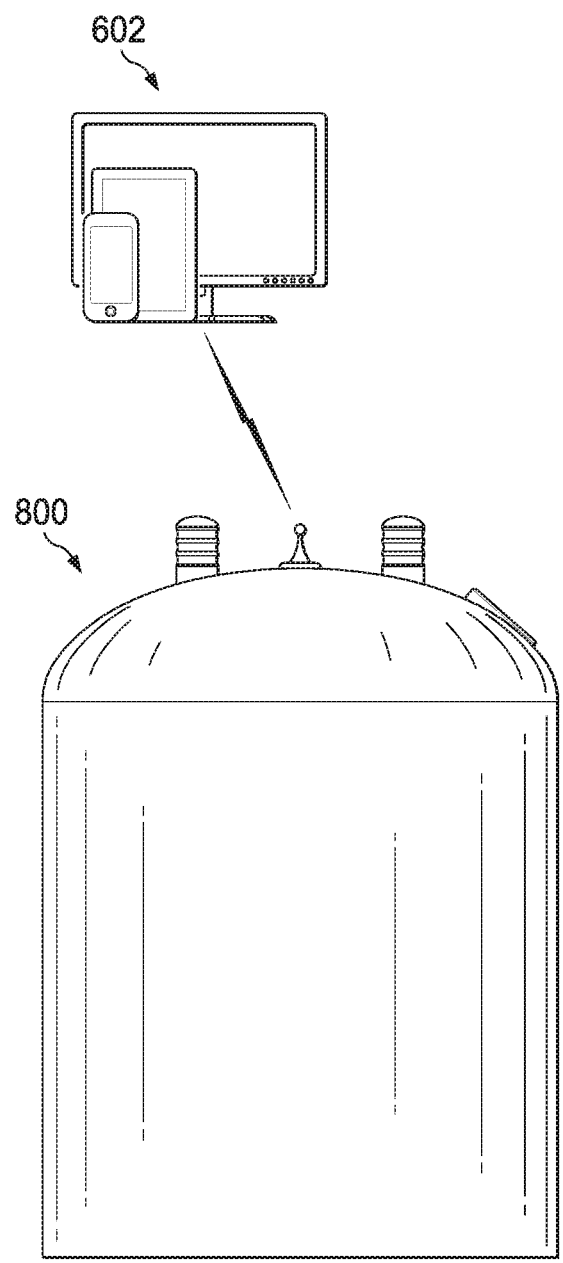
FIG. 15 is a simplified diagram of another exemplary embodiment of an animal care device 800 in operation with a plurality of user computing devices 602 according to the teachings of the present disclosure.

FIG. 15 is a simplified diagram of another exemplary embodiment of an animal care device 800 in operation with a plurality of user computing devices 602 according to the teachings of the present disclosure. A water-tight, hardened, automated and remotely-controlled animal boarding animal care device 800 is designed to withstand all of nature's adverse elements including wind, cold, heat, and flood water. Further contemplated is the use of the care device for detection and protection from harmful environmental substances such as nuclear radiation, and bio, viral, fungal, or chemical agents, to prevent exposure to these toxic agents. The animal care device 800 is equipped with a computer that may automatically initiate pre-programmed functions in response to a potentially hazardous environmental event warning issued by a local, state or federal private or government agency. Although the focus is the protection of pet animals, these devices can be constructed for human use. As described above, the animal care device 800 provides various capabilities useful for providing care to an animal. For example, the animal care device 800 may house a dog, provide shelter, food, water, and medicine. In particular, the animal care device 800 is designed to provide protective shelter in adverse conditions, and shield the animal from harmful environmental conditions, such as floods, hurricanes, tornadoes, toxic or bio-hazardous agents, and even nuclear radiation.

As described above, animal care device 800 is equipped with a bark recognition sensor logic capable of "learning" unique barks or sounds of distress associated with individual animals and differentiating between the barks or distress sounds to determine which individual animal is making the sound, if multiple animals are present and notifying the owner of one-time or continuous dog barking and identifying the dog that is barking. The animal care device 800 is capable of interfacing with and activating personnel or home security system 606 (alarm, directing security cameras toward the sound of the barking, etc.) if the barking exceeds certain parameters (example, constant barking for more than 30 minutes, etc.) and also notifies the owner via a user computing device 602, e.g., cell phone, tablet, or computer, or notify a third person or agency 604. The owner may also issue control and instructions to the animal care device 800 to perform certain functions. The animal care device 800 may take action based on the bark i.e., arming the security system 606, and/or opening a door to allow egress or access to the outside or inside of a building or room. Having the animal care device 800 begin recording when a bark is detected, or alert the owner of a possible threat and allow the owner to view the location via the audio video features of the animal care device 800.

Figure 16:
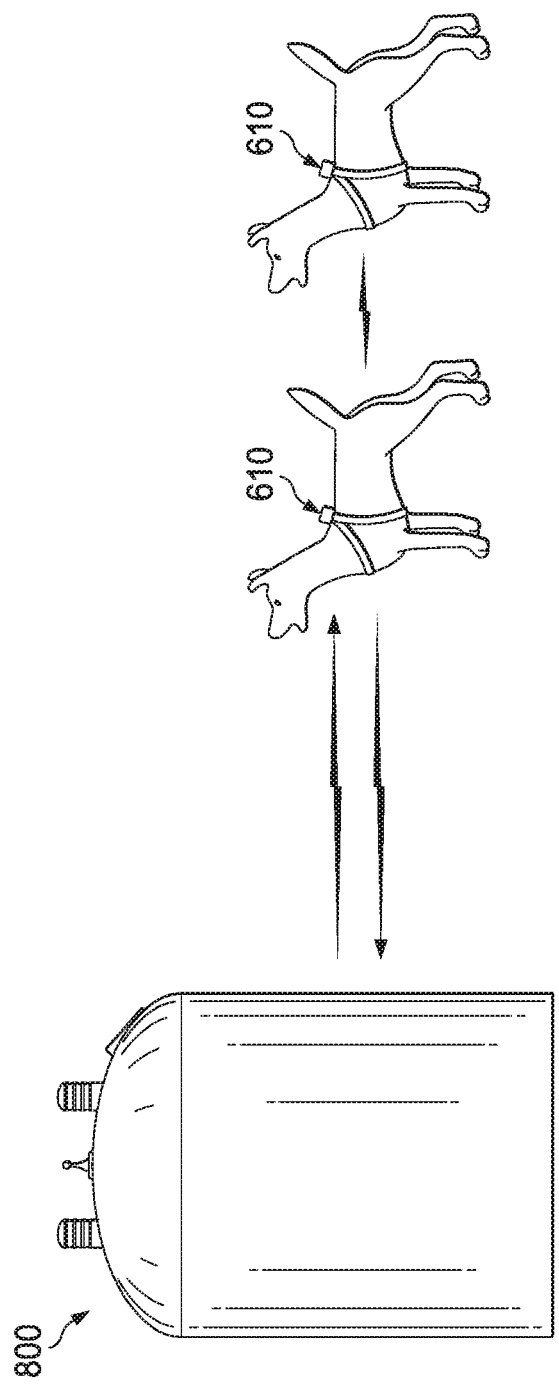
FIG. 16 is a simplified diagram of an exemplary embodiment of an animal care device 800 in operation with a plurality of smart collars/harnesses according to the teachings of the present disclosure.
Figure 17:
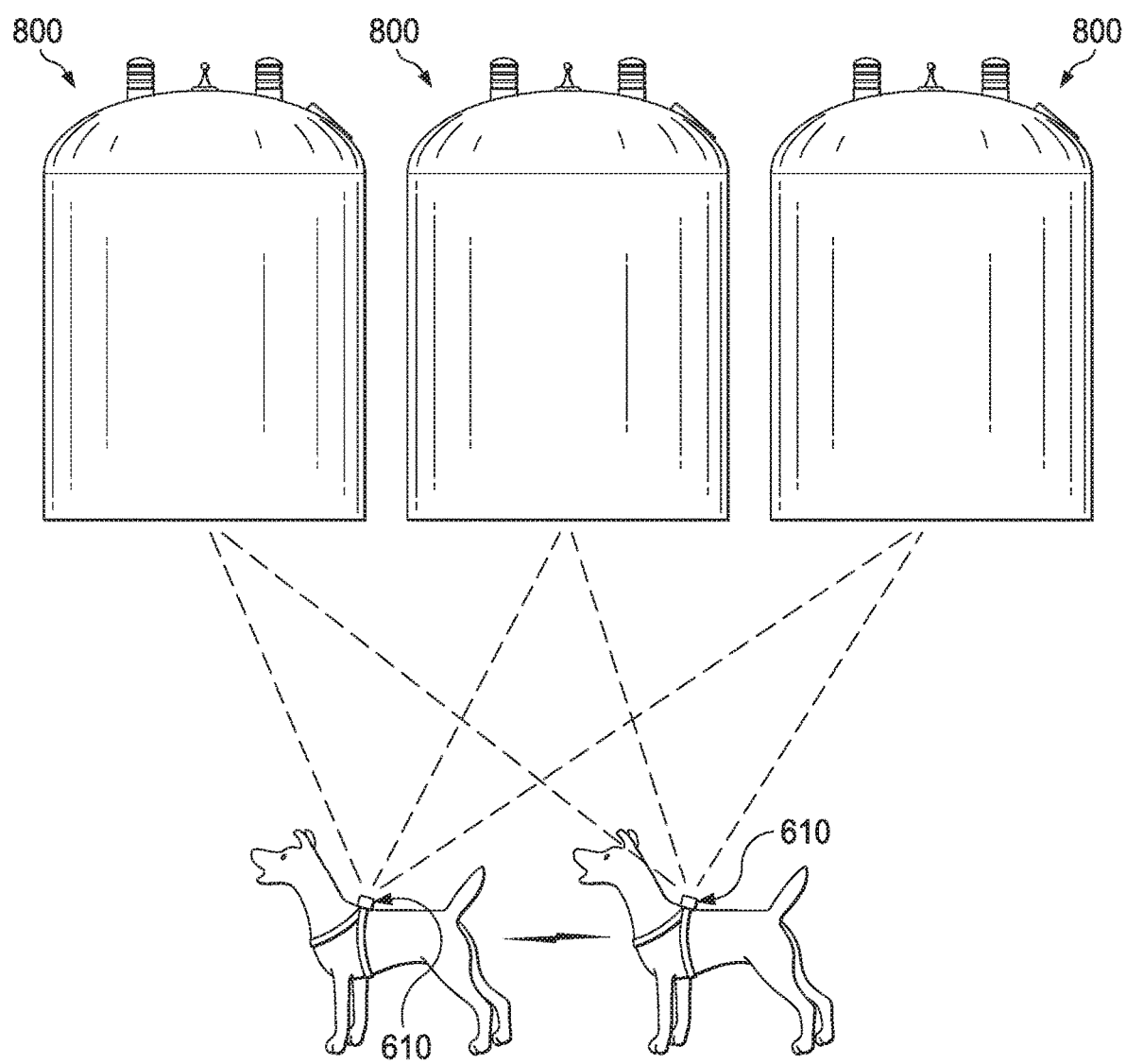
FIGS. 17 and 18 are simplified diagrams of an exemplary embodiment of a plurality of animal care device 800 in operation with a plurality of smart collars/harnesses according to the teachings of the present disclosure.
Figure 18:
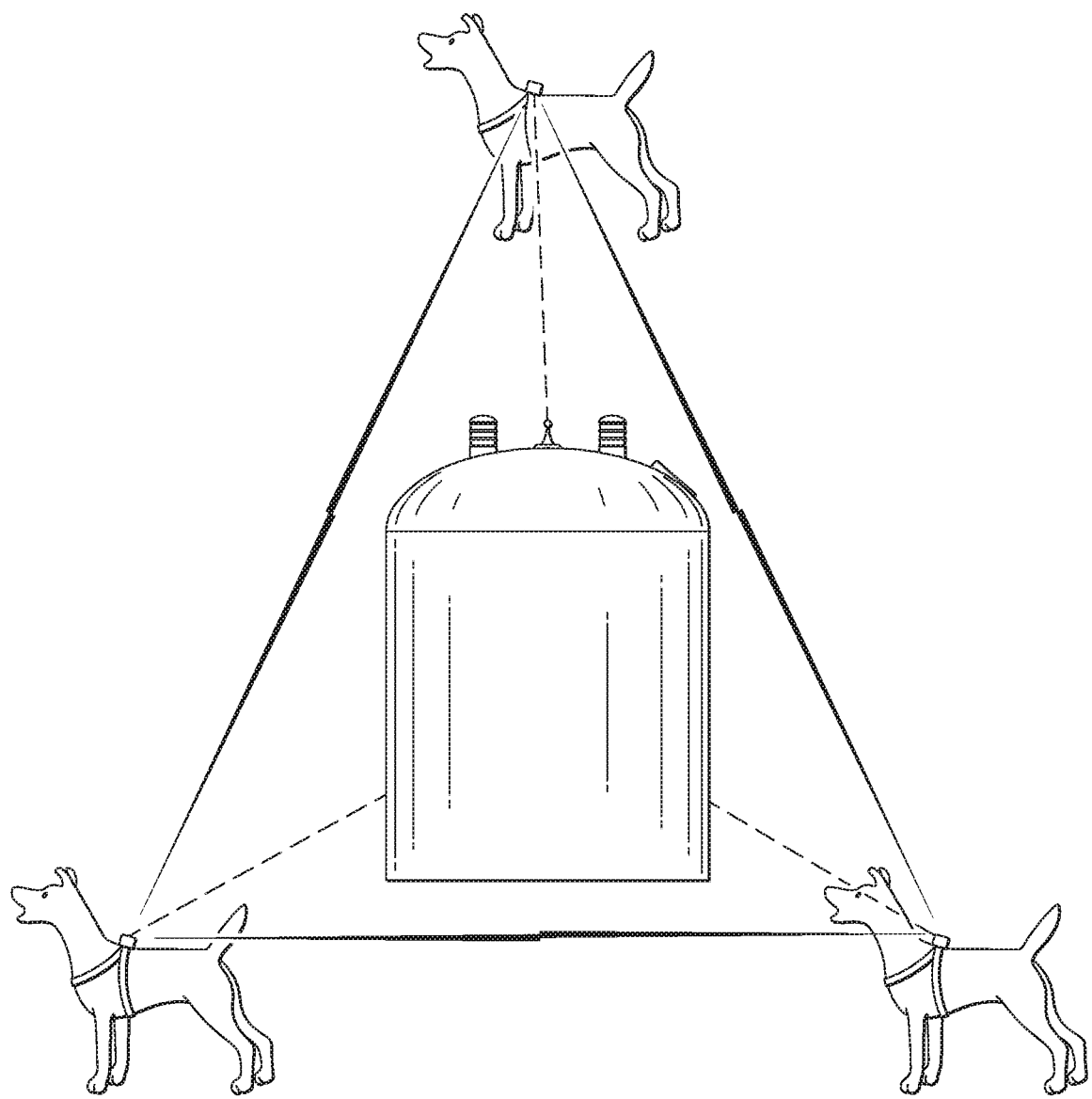

FIG. 16-18 are simplified diagrams of an exemplary embodiment of one or more animal care devices 800 in operation with a plurality of smart collars 608/harnesses 610 according to the teachings of the present disclosure. The system may be configured easily and flexibly to accommodate any number of animal care devices and collars/harnesses. The collar/harness communicates wirelessly with user computing devices, the GPS satellite constellation, cellular telephone network, home security monitoring service, and/or local agencies. Further as described above, the animal care device 800 and/or the smart collar 608 has a camera/video capture component which captures and records the activities of the animal, the environment, and persons/intruders. The smart collar 608 facial recognition component may be interfaced, either directly or via the animal care device 800, or to a system that notifies a remote entity. The smart collar with the on-board camera/video capture device may transmit images to the associated animal care device 800 or a separate database for comparison with known persons who may be missing, wanted by authorities, or in need of assistance. When there are multiple animals wearing smart collars/harnesses present, the collars/harnesses may also communicate among them and relay information where necessary.

The smart collar 608 may be equipped with a hazardous substance or gas detection component that identifies potential air quality threats to the animal 600, other animals or persons in the area so that appropriate action may take place, such as opening the door so that the animal may enter the shelter.

Figure 19:
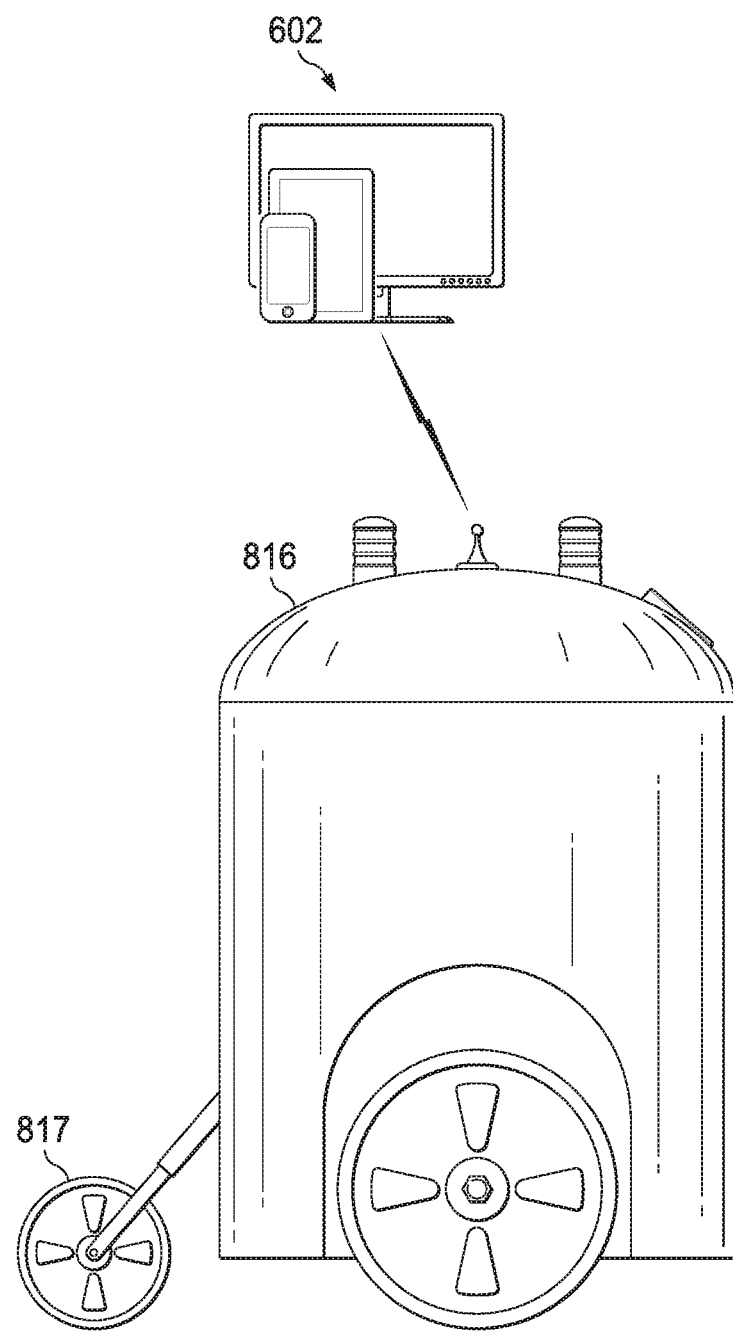
FIG. 19 is a simplified diagram of an exemplary embodiment of a mobile animal care device 816 in operation with a plurality of user computing devices 602 according to the teachings of the present disclosure.
Figure 20:
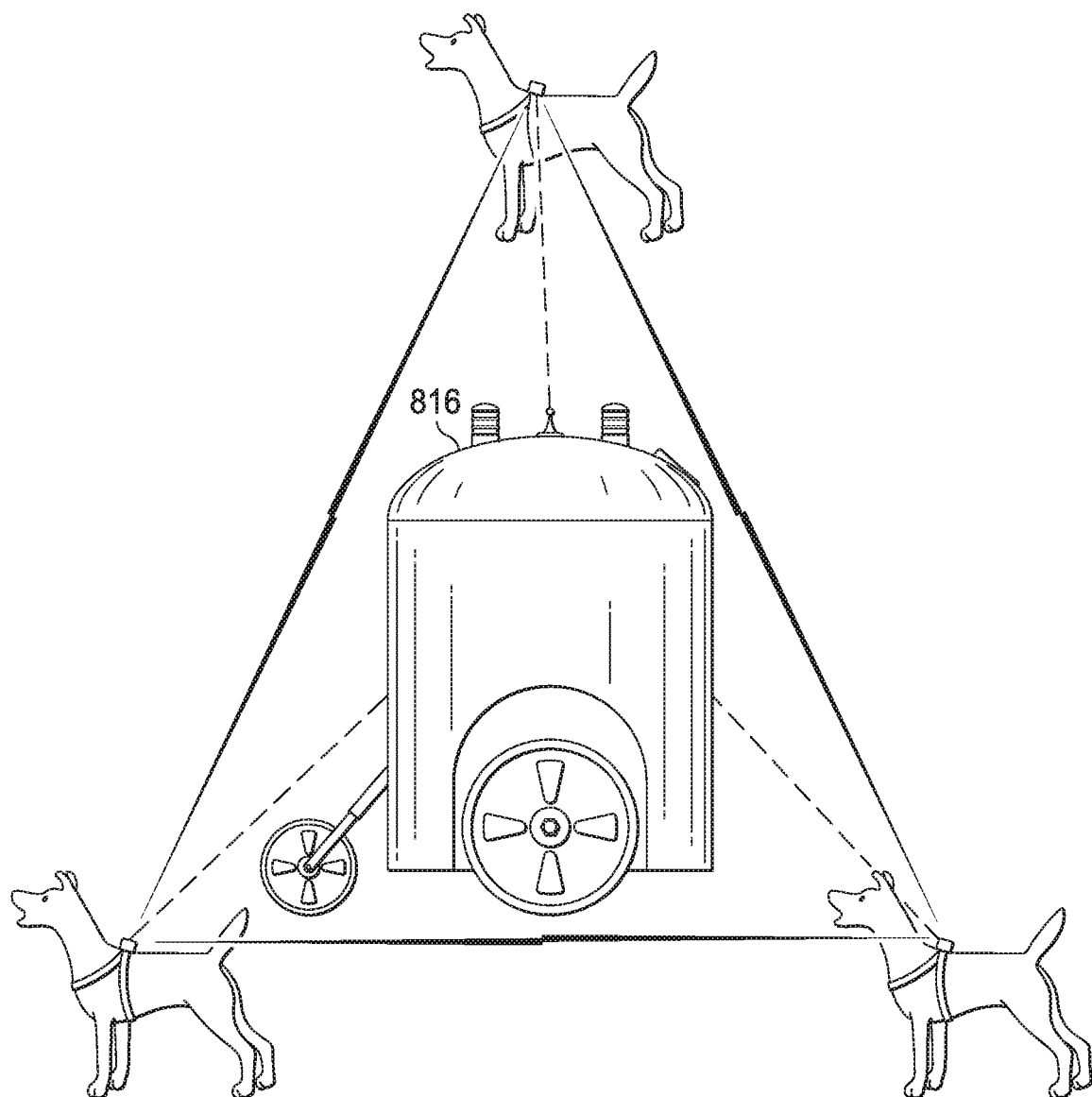
FIG. 20 is a simplified diagram of an exemplary embodiment of a mobile animal care device 816 in operation with a plurality of smart collars/harnesses according to the teachings of the present disclosure.
Figure 21:
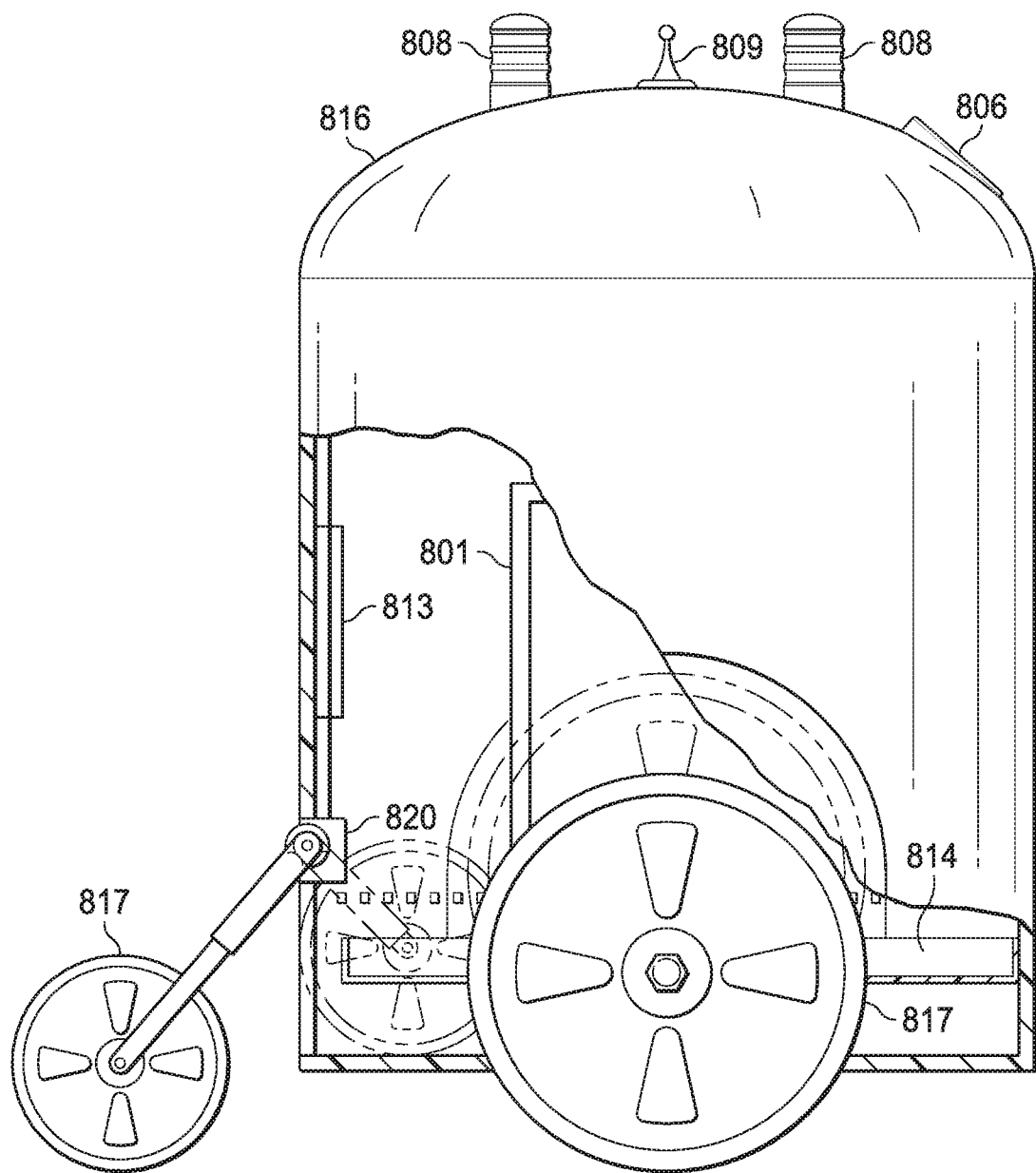
FIG. 21 is a partial cross-sectional side view of an exemplary embodiment of a mobile animal care device 816 according to the teachings of the present disclosure.

FIGS. 19-21 are a simplified diagrams of an exemplary embodiment of a mobile animal care device 816 in operation with one or more user computing devices 602 and/or one or more smart collars/harnesses according to the teachings of the present disclosure. The animal care device 800 includes a mobility portion including wheels 817 that enable it to move about its environment according to instructions issued remotely or by its onboard microprocessor. The wheels 817 preferably can be folded when not in use, and extended when the animal care device is moving about. A motor 820 represents the mechanism that drives retraction of the wheels 817.

The animal care device 800 includes an entrance door 801 that can be shut and sealed once the animal has entered the enclosure pod. The entrance door 801 can be remotely controlled and operated (opened and shut) via wireless communication and mobile devices such as smartphones, laptop computers, and other devices. Once the door is shut, the animal care device 800 provides 360 degrees of sealed protection to an enclosed animal thereby creating a "safety-pod" type enclosure pod to protect from a variety of environmental elements.

Figure 22:
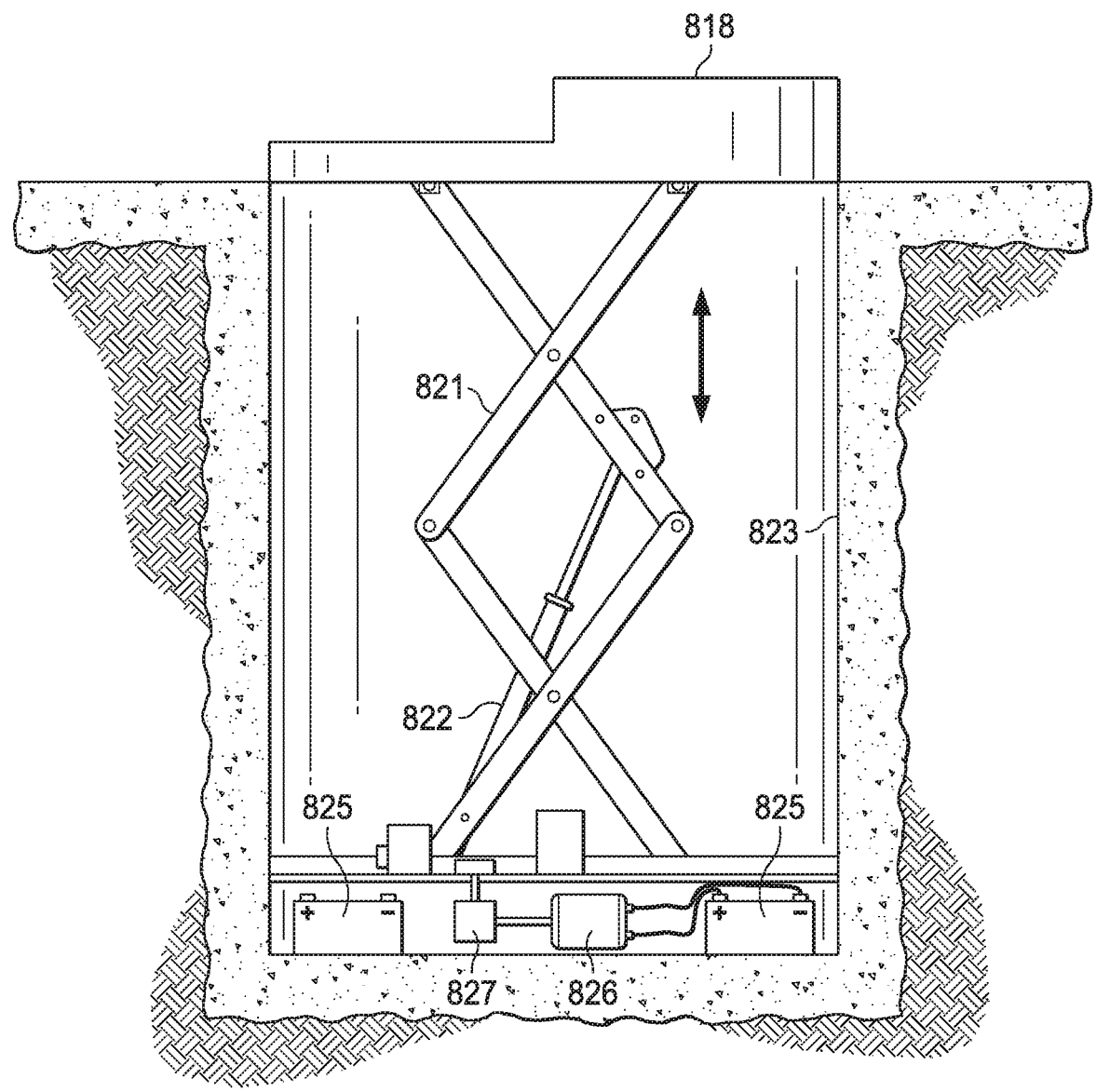
FIGS. 22-24 are cross-sectional side views of an exemplary embodiment of an animal care device 816 with an anchoring and elevation mechanism according to the teachings of the present disclosure.
Figure 23:
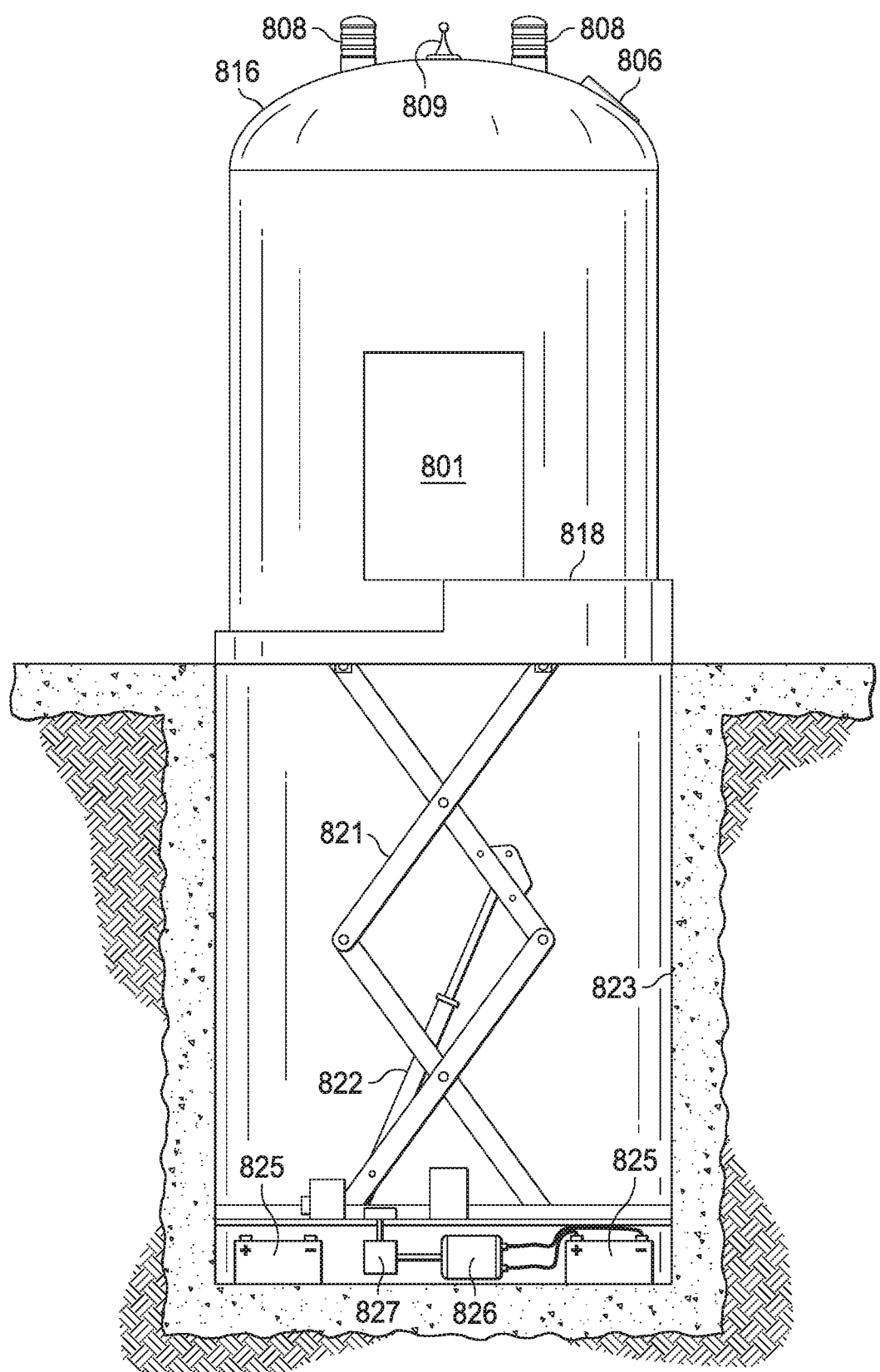
Figure 24:
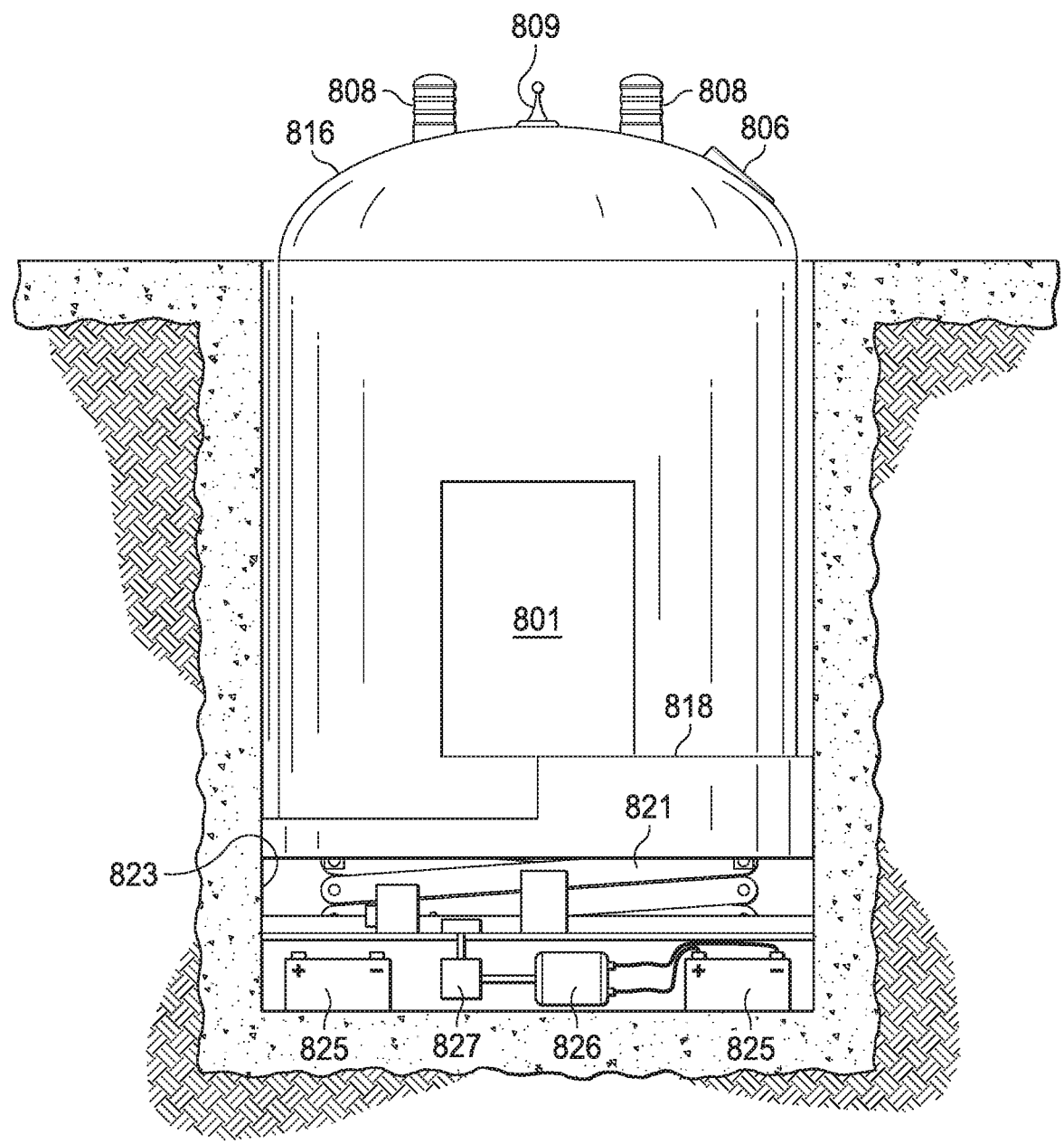

FIGS. 22-24 are cross-sectional side views of an exemplary embodiment of an animal care device 816 with an anchoring and elevation mechanism according to the teachings of the present disclosure. The animal care device 800 is configured to move to its designated anchor spot, and be mounted securely to a firm and solid surface such as a concrete pad and/or dock 818. The animal care device 800 includes a hardened outer shell that could withstand high winds, flying objects and pressure from items that might fall upon it or strike it. It would be insulated to withstand high and low temperature variations. Further, the hardened outer shell may include materials that would block the penetration of nuclear radiation. The animal care device 800 is preferably constructed of a fire-proof or fire-resistant material. The hardened shell defines an inner chamber that can comfortably house and accommodate one or more animals (e.g., dog, cat, bird, etc.).

The animal care device 800 can be raised and lowered into a hardened and secure structure 823 formed in the ground or a separate hardened structure above the ground such as a garage. The raised position permits access to the door of the animal care device, and the lowered position permits further protection by the surrounding structure 823 and the ground. The lowered position is more optimal for protection against a tornado, for example. The elevation mechanism 821 include a motor 826 or another mechanism powered by one or more batteries 825. The power system may also include connection to the electric grid and to a wind and/or solar generator. The elevation mechanism may include pneumatic, hydraulic, and other conventional components 822. The motor 826 is preferably in communication with the computer controller to enable remote control of its operations, preferably via user computing devices such as a smartphone. The elevation mechanism 821 may also be activated on-site by one or more user interfaces coupled to the computer controller.

Figure 25:
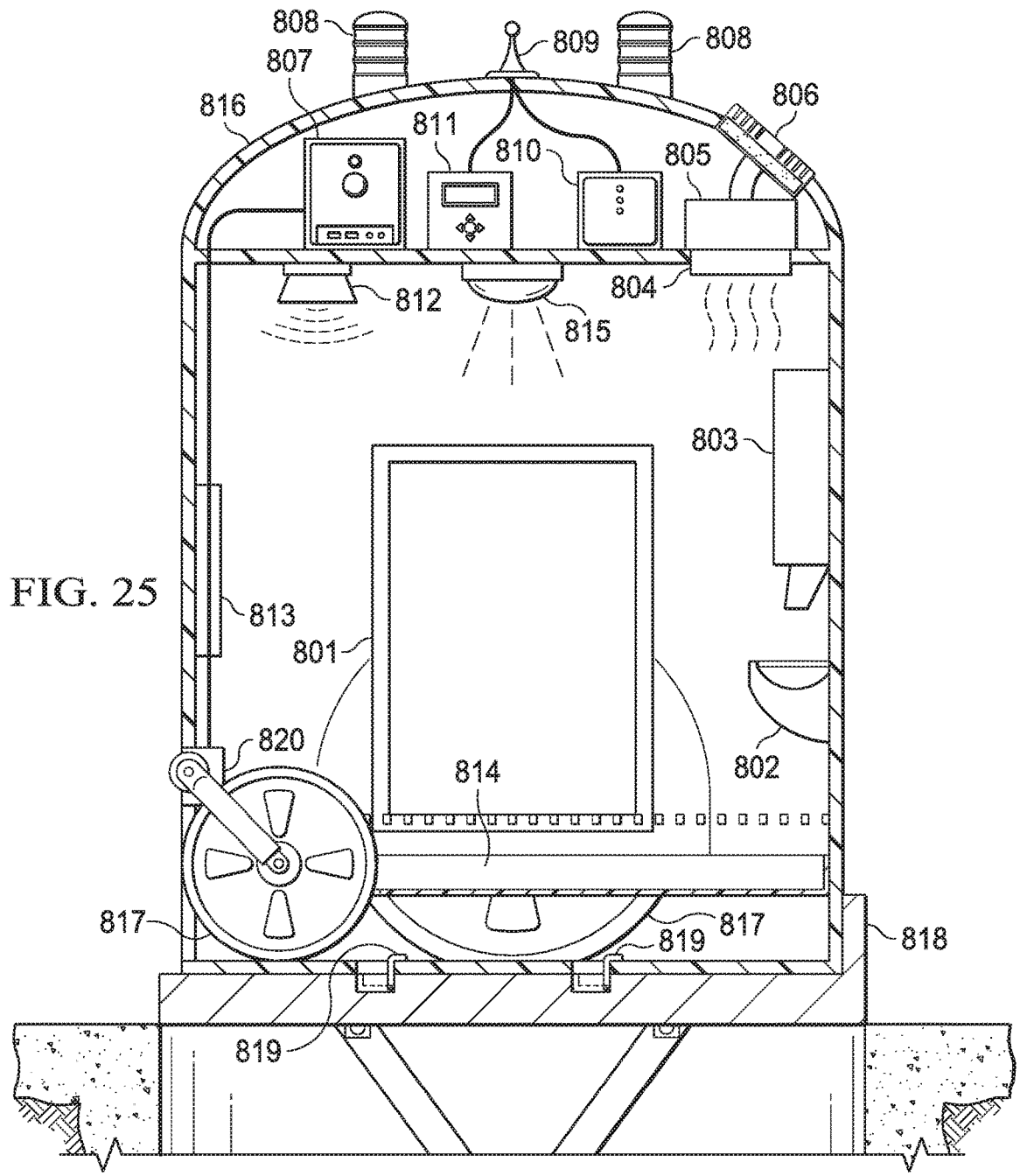
FIG. 25 is a more detailed cross-sectional side view of an exemplary embodiment of a mobile animal care device 816 with an elevation mechanism according to the teachings of the present disclosure.

Referring also to FIG. 25, when the animal care device 800 is lowered into the ground, a purified air supply system 806 supplies fresh and filtered air to a heating/cooling system 804 and 805. The air may be supplied from outside of the device or the device may be equipped with a certain quantity of air supply (e.g., air tanks). The computer controller 507 and a thermostat are programmed to automatically sense the interior temperature and air quality so that the interior environment of the animal care device 800 is regulated to ensure comfort of the occupant. The animal care device 800 may also include a variety of sensors that may sense the outside environmental conditions for communications to a remote user. For example, the sensors may detect that the pod is underwater, experiencing high temperatures (possibly indicating fire hazard), or that certain harmful agents, such as carbon dioxide, carbon monoxide, and other poisonous substances, are present. The computer controller 507 is programmed with decisions and logic to consider these factors to maintain the safety of the occupant. The computer controller 507 is coupled to a user interface that enables input of commands and instructions and display of status and other data. For example, the pod may be raised in case of flood, ventilation or oxygen stores may be activated or increased in the presence of certain hazardous gases, fire retardant chemicals may be released in case of fire, etc. Further, automatic notification of the owner, private security firms, or government emergency response agencies may be transmitted when appropriate.

The animal care device 800 further includes a self-contained automated feeding and watering food/water/medicine dispenser 803 and tray 802. The dispenser 803 includes a sensor that detects whether the food tray and/or the water tray need to be replenished, and a computer controller 807 that is configured to dispense pre-portioned amount of food and water as necessary. The food and water dispenser may alternatively operate based on a pre-programmed schedule, and further subject to remote-control by the user. The automated system is powered by a power supply such as one or more batteries 825, that can be powered by the electric grid, and solar and/or wind generators.

The animal care device 800 also includes a GPS beacon 811 or another type of electronic location positioning technology capable of emitting and receiving signals so that the presence and location of the enclosure pod can be quickly determined to effect a rescue. The animal care device 800 may also include at least one light source 815 as well as a display monitor and camera device 813 (including speakers and a microphone) to allow for two-way image and audio communication between the animal and a remotely-located user via the Internet or other communication networks. The lighting system 815 can be regulated (brightened and dimmed) by the computer controller 807 to simulate day and night cycles. This lighting system is designed to regulate the animal's internal biological clock to allow the animals eating, sleeping and other habits to not be adversely affected. The animal care device 800 may also include a smart collar or another device to measure vital signs (pulse, temperature, etc.) of the animal and communicate this information to the remote user. The communication system may include an antenna 809 and a modem or transceivers 810 to enable the sending and receiving of data.

The animal care device 800 would also be capable of emitting a bright light such as a strobe light 808, audible noise (siren), or specialized scent to allow the animal care device 800 to be located by third parties or other animals. The animal care device 800 preferably include a waste containment system 814 designed to allow waste materials and debris such as feces and urine to pass through a structure such as a grate disposed at the bottom of the enclosure pod to a holding chamber that collect and store the waste. The waste containment system 814 may further include mechanism to discharge the waste from the pod when conditions permit.

The animal care device 800 preferably includes a play element or toy to allow the dog or another animal to remain occupied and alert. The animal care device 800 may also have the capability of playing pre-programmed messages and/or images stored in a memory accessible by the computer controller 807 on a predetermined time schedule or remotely activated basis.

Figure 26:
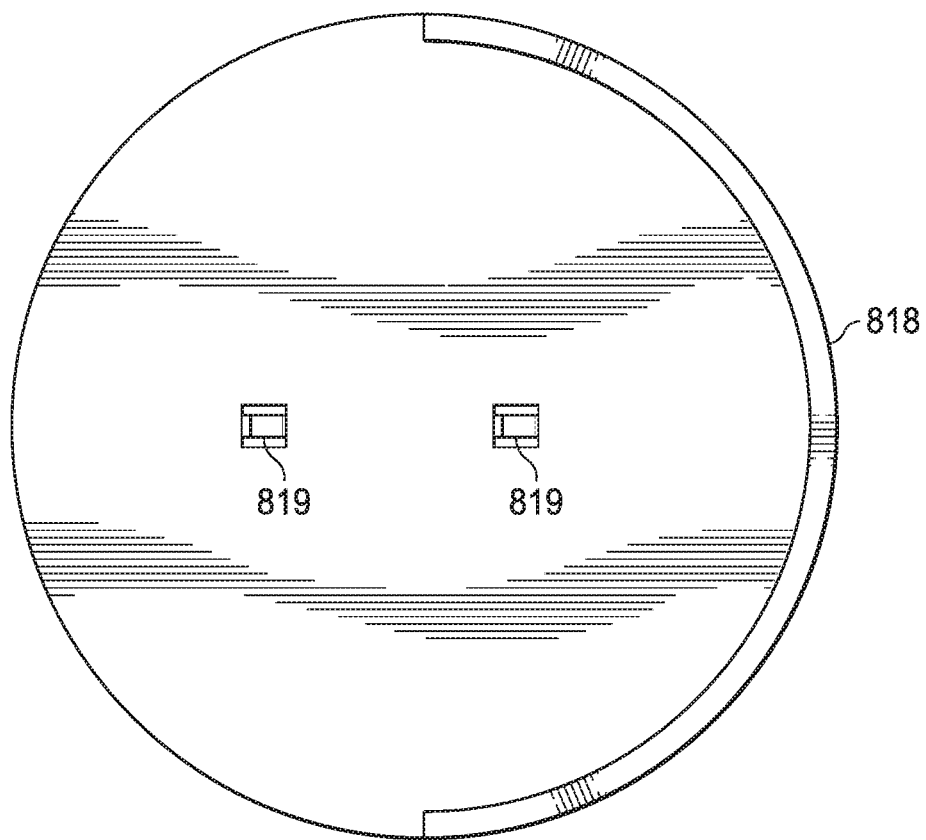
FIG. 26 is a top view of an exemplary embodiment of the locking pins 819 according to the teachings of the present disclosure.
Figure 27:
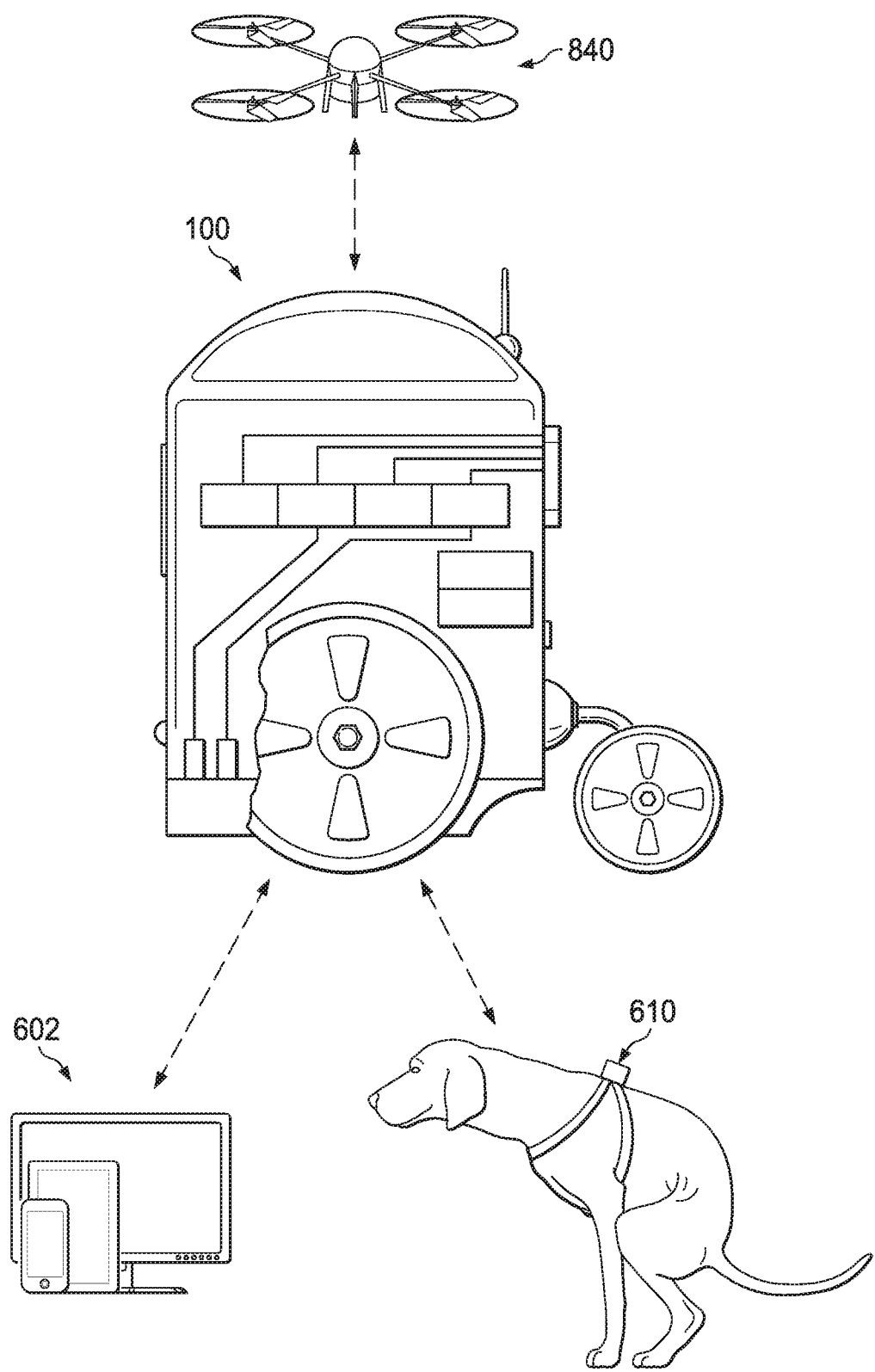
FIGS. 27-32 are diagrams of exemplary embodiment of a mobile animal care device operating cooperatively with one or more drones 840 according to the teachings of the present disclosure.
Figure 28:
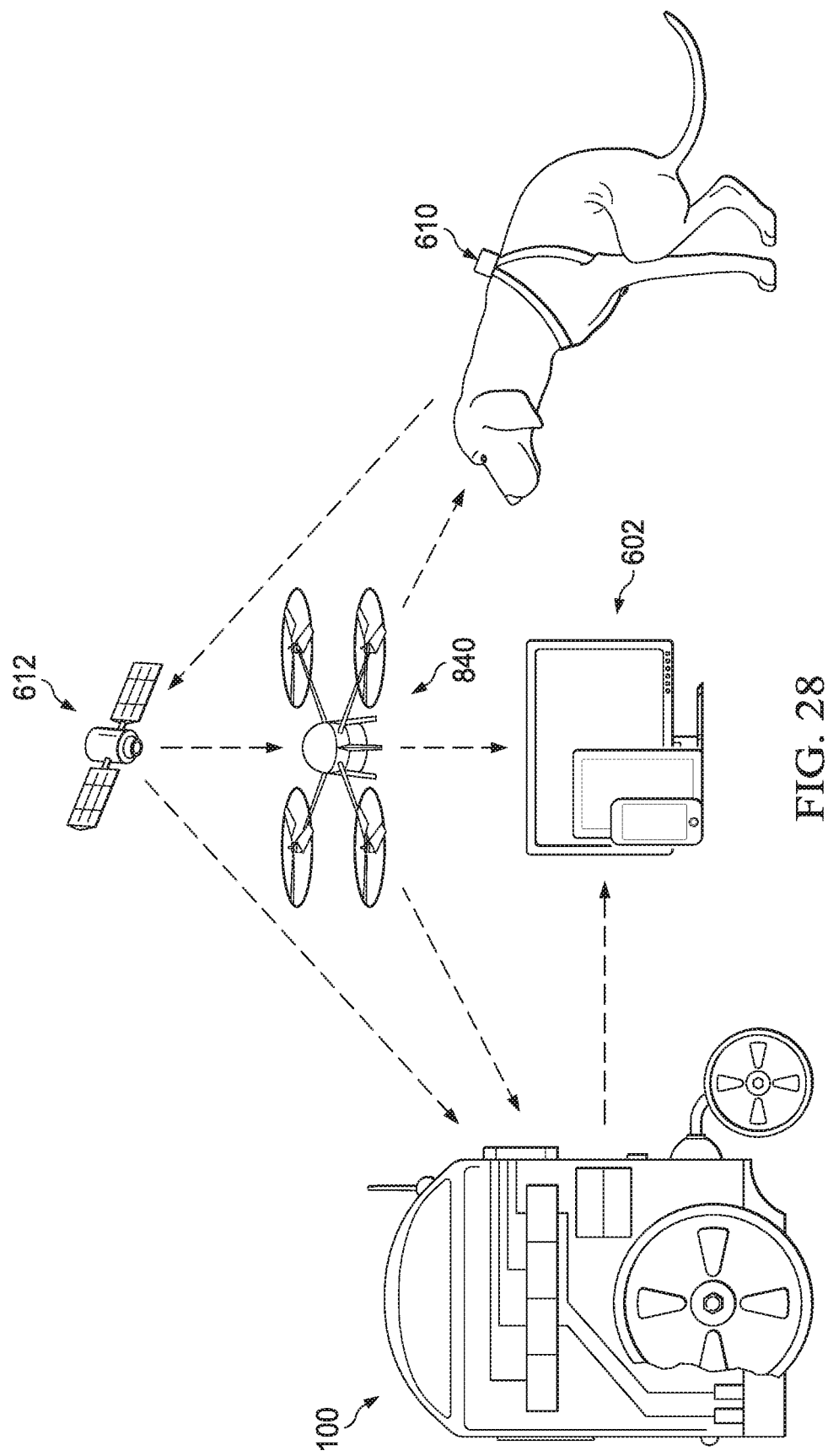
Figure 29:
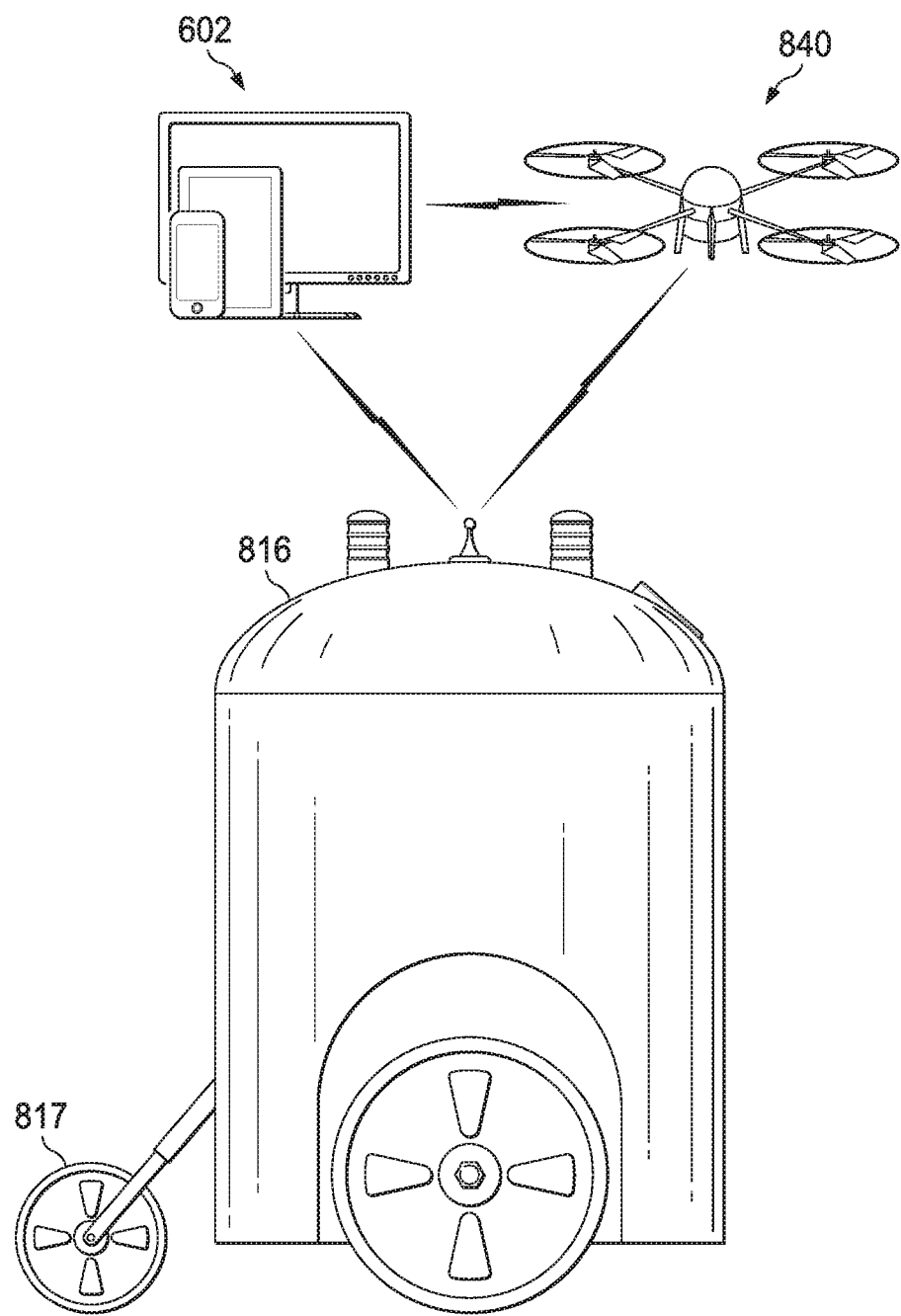
Figure 30:
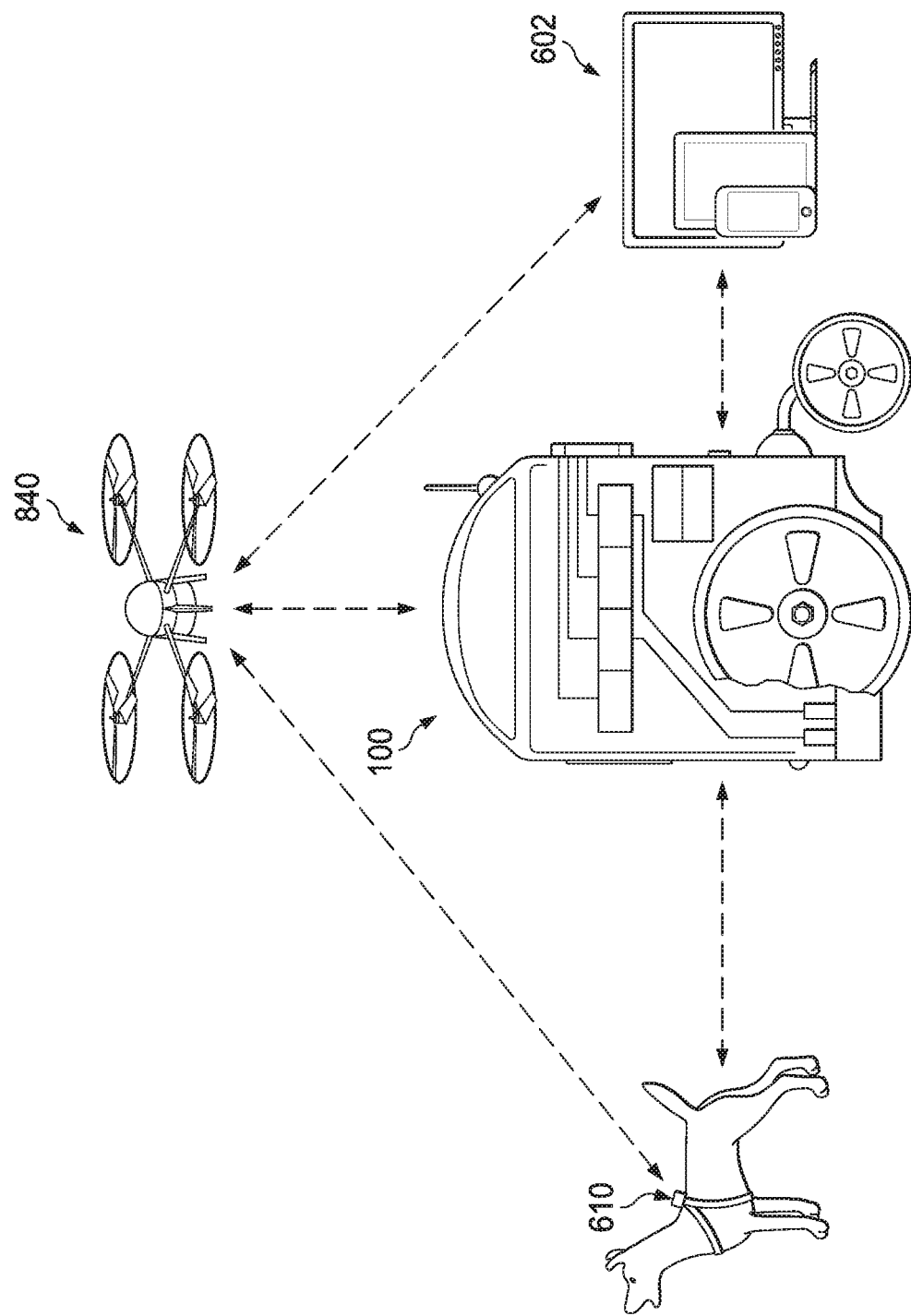
Figure 31:
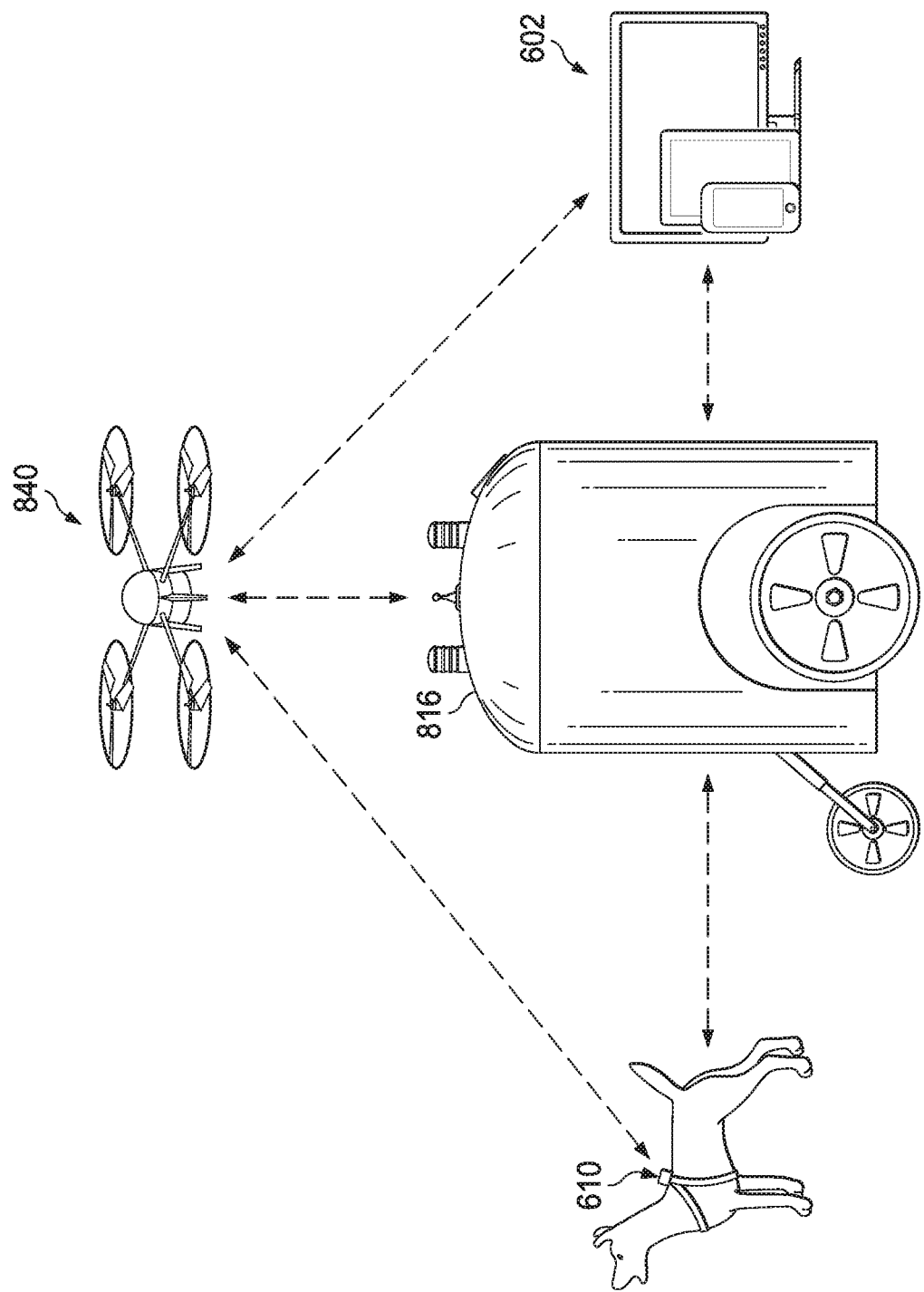
Figure 32:
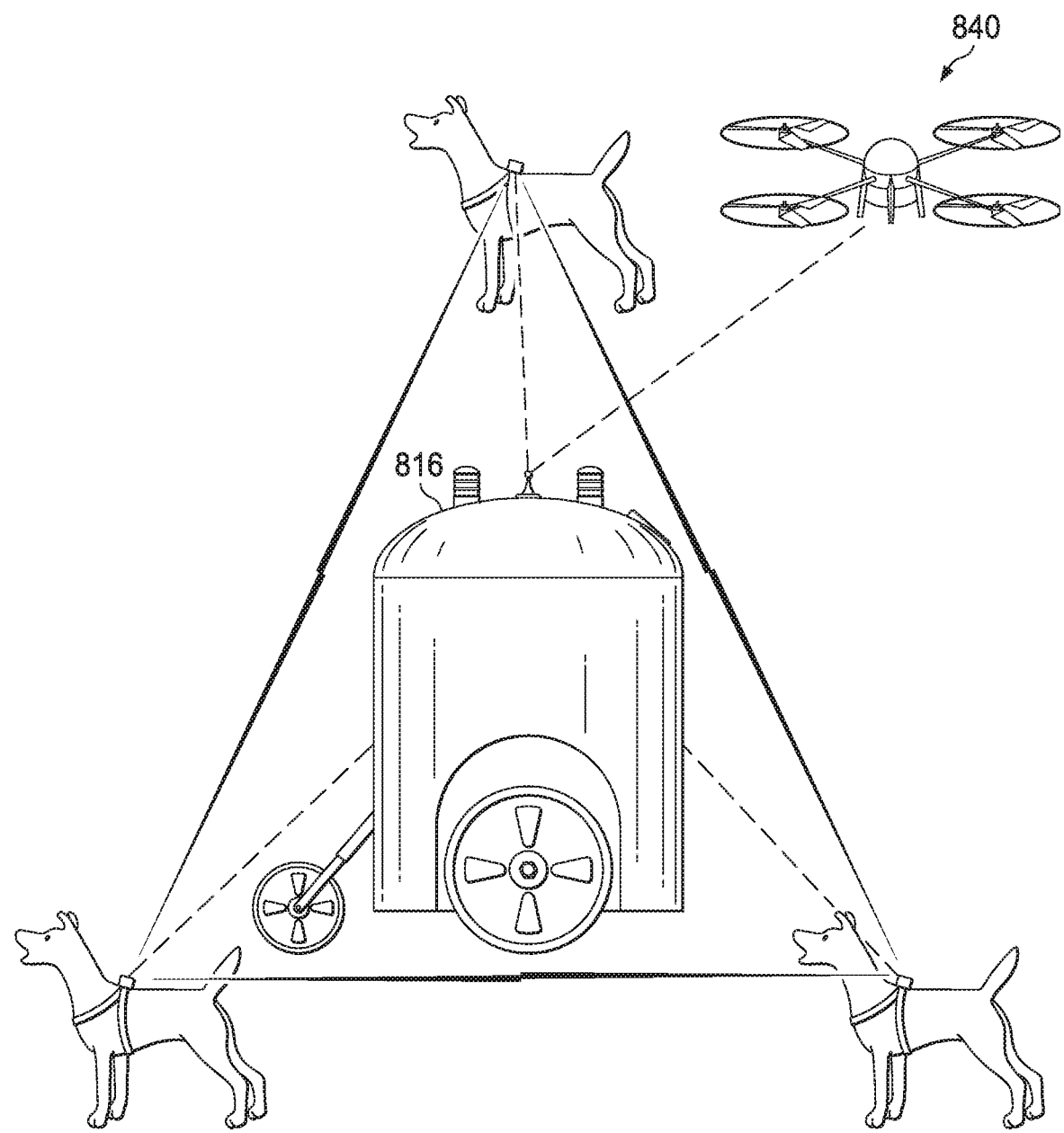

FIG. 26 is a top view of an exemplary embodiment of the locking pins 819 according to the teachings of the present disclosure. The locking pins 819 is one type of anchoring mechanism that may be used to securely fasten the animal care device to the concrete structure so that it remains in place despite strong winds and flood waters.

FIGS. 27-32 are diagrams of exemplary embodiment of a mobile animal care device 900 operating cooperatively with one or more unmanned aerial drones 840 according to the teachings of the present disclosure. An aerial drone 840 is an unmanned aerial vehicle that can be controlled remotely by a human operator or can navigate autonomously real-time using on-board or remote GPS, on-board flight controller, and artificial intelligence (on-board or remote). The aerial drone 840 includes one or more on-board cameras that are capable of capturing images and sounds in real-time from one or more perspectives. The aerial drone 840 further has a wireless communication module that enable it to wirelessly and bi-directionally communicate with the mobile animal care device 900, user computing devices 602, smart collars 610 worn by the animals, navigational satellites (GPS), and other aerial drones. Data, including position, orientation, commands, video, and audio are transmitted and received by the aerial drone 900 using wireless communication. The aerial drone and/or the animal care device are also capable of communicating with remote databases, servers and/or networks to receive instructions/commands, threat and weather notifications, software updates, and other information, as well as access and store data. Preferably the data transmitted over the wireless communication channel are encrypted to prevent unauthorized access. The aerial drone 840 may also incorporate a plurality of position and movement sensors that provide additional information about its absolute or relative position and orientation. The aerial drone may also be capable of broadcasting live or recorded audio information, such as the owner's verbal commands, praises, and reassurances to the animal(s). Further, the aerial drone may include a projector that enable it to project a live or recorded video feed, images, and/or holograms for viewing by the animal(s). The aerial drone 840 may have various form factors such as mono-copter, bi-copter, quadcopter, octocopter, etc. and tailed or tailless designs.

In operation, the mobility portion of the animal care device can navigate and move according to instructions issued by its on-board microprocessor. The microprocessor in turn is configured to generate navigational and operational instructions in response to a variety of sensory inputs as described above, including geo-location information from the smart collar(s), drone sensory inputs, and images captured by the on-board camera(s) of the aerial drone 900. The aerial drone 900 is also configured to operate (e.g., take-off, land, flight according to a predetermined pattern, and flight according to GPS navigation), in response to instructions issued by the microprocessor of the animal care device and transmitted over the wireless communication channel. The microprocessor is operable to instruct the aerial drone to navigate in a predetermined pattern and perform, for example, urging the animal to move in a certain direction, fetch and provide food, fetch and provide water, fetch and provide medicine, and fetch and provide a play element.

The aerial drone is further configured to generate video or still image data of a survey area, which are transmitted to the microprocessor of the animal care device for analysis. The microprocessor is configured to generate a map of the survey area and instructions for the aerial drone to navigate within the survey area according to the map. The microprocessor is also configured to perform functions such as facial recognition, location recognition, threat detection, animal welfare analysis, defecation detection, defecation removal, and terrain analysis by using image data received from the aerial drone(s). Further contemplated is the use of the aerial drone for detection and protection from harmful environmental substances such as nuclear radiation, and bio, viral, fungal, or chemical agents, to prevent exposure to these toxic agents. The aerial drone may automatically contact relevant agencies in response to detecting a harmful situation, such as contacting public safety and firefighting agencies. The aerial drone is equipped with a computer that may automatically initiate pre-programmed functions in response to a potentially hazardous environmental event warning issued by a local, state or federal private or government agency. The aerial drone is equipped with the necessary sensors and detectors, combined with video cameras to enable the detection of hazards and transmit the information to the animal care device as well as relevant agencies.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention may be described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational actions to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A system for remote care of an animal comprising:
a robotic animal caregiver including:
a housing;
a wireless data communication system disposed within the housing and wirelessly communicatively coupled with an external data communications system; and
a microprocessor in communication with the wireless data communication system disposed within the housing;
an aerial drone wirelessly communicatively coupled to the wireless data communication system of the robotic animal caregiver, the aerial drone comprising a microprocessor, a wireless communication module, a video camera, the aerial drone configured to act in response to instructions issued by the microprocessor of the robotic animal caregiver; and
wherein at least one of the robotic animal caregiver and the aerial drone comprises a dispenser configured to dispense at least one of food, water, and medication according to a pre-programmed schedule.

2. The system of claim 1, further comprising a mobility portion coupled to the housing and configured to move the housing in response to control instructions issued by the microprocessor.

3. The system of claim 1, further comprising a smart collar to be worn by the animal operable to determine a geo-location and behavior information of the animal and communicate with the microprocessor.

4. The system of claim 3, wherein the smart collar is operable to transmit the geo-location and behavior information of the animal to the microprocessor, the microprocessor is operable to determine that the animal has defecated at a deposit location in response to analyzing the geo-location and behavior information of the animal, and the microprocessor being operable to instruct the aerial drone to navigate to the deposit location to collect feces deposited by the animal.

5. The system of claim 3, wherein the aerial drone is configured to communicate wirelessly with the smart collar, determine a geo-location of the animal in real-time, and transmit the geo-location of the animal to the microprocessor of the robotic animal caregiver.

6. The system of claim 3, wherein the aerial drone is configured to communicate wirelessly with a plurality of smart collars worn by a plurality of animals, determine a geo-location of the plurality of animals in real-time, and transmit the geo-location of the plurality of animals to the microprocessor of the robotic animal caregiver.

7. The system of claim 3, further comprising a plurality of aerial drones wirelessly communicatively coupled to a plurality of smart collars worn by a plurality of animals, the aerial drone comprising a microprocessor, a wireless communication module, a video camera, the plurality of aerial drones configured to act in response to data received from the smart collars.

8. The system of claim 1, wherein the video camera of the aerial drone captures images in response to instructions issued by the microprocessor of the robotic animal caregiver.

9. The system of claim 1, wherein the aerial drone is operable to capture at least one image of the animal in real-time, determine a geo-location of the animal in real-time, and transmit the geo-location of the animal to the microprocessor of the robotic animal caregiver.

10. The system of claim 1, wherein the aerial drone is operable to capture at least one image of the animal, and transmit the at least one image of the animal to the microprocessor of the robotic animal caregiver for automatically performing at least one of: facial recognition, location recognition, threat detection, hazard detection, emergency notification, animal welfare analysis, defecation detection, defecation removal, and terrain analysis.

11. The system of claim 1, wherein the microprocessor of the aerial drone is operable to instruct the aerial drone to navigate in a predetermined pattern.

12. The system of claim 1, wherein the microprocessor of the aerial drone is operable to instruct the aerial drone to navigate in a predetermined pattern and perform at least one of: urging the animal to move in a certain direction, fetch and provide food, fetch and provide water, fetch and provide medicine, and fetch and provide a play element.

13. The system of claim 1, wherein the aerial drone is configured to generate video data of a survey area, the microprocessor of the robotic caregiver being operable to receive and analyze the video data and generate a map of the survey area and to instruct the aerial drone to navigate within the survey area according to the map.

14. The system of claim 1, wherein the housing comprises a water-tight housing with a hardened structural shell defining the chamber for accommodating the animal.

15. The system of claim 14, further comprising a docking mechanism operable to automatically secure the housing to a fixed structure to prevent undesirable movement as controlled by the microprocessor.

16. The system of claim 14, further comprising an air supply system configured to provide sufficient life-sustaining air to the chamber, the air supply system being automatically controlled by the microprocessor in response to remote instructions transmitted via the wireless data communications system.

17. The system of claim 14, further comprising a motorized elevation mechanism configured to automatically lower and raise the water-tight housing subterraneously controlled by the microprocessor.

18. The system of claim 14, further comprising an elevation mechanism configured to automatically lower and raise the water-proof housing subterraneously controlled by the microprocessor in response to remote instructions transmitted via the wireless data communications system.

19. The system of claim 14, further comprising an above-ground enclosure configured for securely containing the water-tight housing.

20. A method for remote care of an animal using a robotic animal caregiver and an aerial drone, comprising: receiving real-time geo-location and behavior information of the animal from a smart collar worn by the animal; receiving image data of the animal from the aerial drone; determining an action to be taken by the robotic animal caregiver at a certain location; and issuing instructions to the robotic animal caregiver to navigate to the certain location and perform the action including dispensing at least one of food, water, and medication.

21. The method of claim 20, further comprising receiving geo-locations and behavior information of a plurality of animals from a plurality of smart collars worn by the animals.

22. The method of claim 20, further comprising receiving at least one of real-time image data of the animal captured by the aerial drone, and real-time sensory data of the animal's surroundings sensed by the aerial drone.

23. The method of claim 22, further comprising performing at least one of facial recognition, location recognition, threat detection, hazard detection, emergency notification, animal welfare analysis, defecation detection, defecation removal, and terrain analysis in response to the received real-time image data of the animal.

24. The method of claim 22, further comprising automatically lowering the robotic animal caregiver subterraneously in response to receiving the real-time sensory data captured by the aerial drone.

25. The method of claim 22, further comprising automatically lowering the robotic animal caregiver subterraneously in response to receiving the real-time image data captured by the aerial drone.

26. The method of claim 22, further comprising automatically and securely docking the robotic animal caregiver in response to receiving the sensory data captured by the aerial drone.

27. The method of claim 26, further comprising automatically and securely docking the robotic animal caregiver in response to receiving the real-time image data captured by the aerial drone.

28. The method of claim 20, further comprising receiving real-time image data of a survey area captured by the aerial drone.

29. The method of claim 28, further comprising generating and transmitting navigation instructions to the aerial drone in response to the received real-time image data.

30. The method of claim 28, further comprising generating and transmitting instructions to the aerial drone to perform at least one of: urging the animal to move in a certain direction, fetch and provide food, fetch and provide water, fetch and provide medicine, and fetch and provide a play element in response to the received real-time image data.

31. The method of claim 20, further comprising determining that the animal has defecated at a deposit location in response to analyzing the geo-location and behavior information of the animal.

32. The method of claim 31, further comprising navigating one of the robotic caregiver and the aerial drone to the deposit location to collect feces deposited by the animal.

* * * * *